(12) United States Patent
Jenkinson

(10) Patent No.: US 6,485,495 B1
(45) Date of Patent: Nov. 26, 2002

(54) CORRUGATED OSTEOTOME BLADE AND METHOD OF SEVERING BONES AND OTHER ANATOMICAL STRUCTURES

(75) Inventor: Edwin O. Jenkinson, Covington, LA (US)

(73) Assignee: Surgical Specialties Puerto Rico, Inc., Reading, PA (US)

( * ) Notice: Subject to any disclaimer, the term of this patent is extended or adjusted under 35 U.S.C. 154(b) by 0 days.

(21) Appl. No.: 09/564,467

(22) Filed: May 3, 2000

Related U.S. Application Data

(60) Provisional application No. 60/133,880, filed on May 12, 1999.

(51) Int. Cl.[7] ............................................. A61B 17/00
(52) U.S. Cl. ........................................ 606/84; 606/167
(58) Field of Search ............................ 606/79, 82, 84, 606/167, 169, 171, 172, 176, 177, 178, 184, 185; 30/277.4, 167, 355, 315, 305, 277, 329, 337, 339, 340, 344, 346.56

(56) References Cited

U.S. PATENT DOCUMENTS

| | | |
|---|---|---|
| 1,504,501 A | 8/1924 | Pope |
| 2,309,814 A | 2/1943 | Youngberg |
| 2,487,221 A | 11/1949 | Cooke |
| 2,630,627 A * | 3/1953 | Beck |
| 2,799,929 A | 7/1957 | Kurianski |
| 3,986,512 A | 10/1976 | Walliser |
| 4,150,675 A | 4/1979 | Comparetto |
| 4,349,018 A | 9/1982 | Chambers |
| 4,349,058 A | 9/1982 | Comparetto |
| 4,433,681 A | 2/1984 | Comparetto |
| 4,457,070 A * | 7/1984 | Reeves ............... 30/314 |
| 4,501,268 A | 2/1985 | Comparetto |
| 4,502,474 A | 3/1985 | Comparetto |
| 4,586,496 A | 5/1986 | Keller |
| 4,627,425 A | 12/1986 | Reese |
| 4,632,102 A | 12/1986 | Comparetto |
| 4,657,002 A | 4/1987 | Ray |
| 4,664,102 A | 5/1987 | Comparetto |
| 4,708,133 A | 11/1987 | Comparetto |
| 4,728,330 A | 3/1988 | Comparetto |
| 4,750,481 A | 6/1988 | Reese |
| 4,881,534 A | 11/1989 | Uhl et al. |
| 4,944,744 A | 7/1990 | Ray |
| 4,952,214 A | 8/1990 | Comparetto |
| 4,959,066 A | 9/1990 | Dunn et al. |
| 5,035,698 A | 7/1991 | Comparetto |
| 5,095,875 A * | 3/1992 | Morris et al. ............... 83/856 |
| 5,147,364 A | 9/1992 | Comparetto |
| 5,665,090 A | 9/1997 | Rockwood et al. |
| 5,683,406 A | 11/1997 | Altobelli et al. |
| 5,722,977 A | 3/1998 | Wilhelmy |
| 5,743,915 A | 4/1998 | Bertin et al. |

* cited by examiner

Primary Examiner—David O. Reip
(74) Attorney, Agent, or Firm—Piper Rudnick

(57) ABSTRACT

A corrugated blade is utilized to form corrugated patterns in ends of a severed bone. The corrugated patterns enable the severed bone sections to be coupled in a mated fashion, thereby providing increased contact area between the bone sections and enhanced stability to promote healing. Further, the corrugated patterns may be offset when coupling the severed bone sections together in order to adjust the bone length and/or orientation to correct a deformity. The corrugated blade may be configured in various fashions (e.g., left or right curve, curved upward or downward, arcuate, etc.) to facilitate manipulation of severed sections into a desired position or orientation. The corrugated blade may be attached to an osteotome handle for manual use, or may be adapted to engage a power tool or saw to sever the bone. Moreover, the corrugated blades may be utilized for other anatomical structures (e.g., veins, arteries, soft tissue, bowels, etc.) to provide a mated fit between severed sections and promote healing as described above. The corrugated blade may further be configured in the form of a bone staple and inserted into bone sections to enhance the connection between those sections. The staple includes perforations to permit the staple to remain within the bone, and various openings to permit the bone to grow through the holes to reinforce the connection.

39 Claims, 16 Drawing Sheets

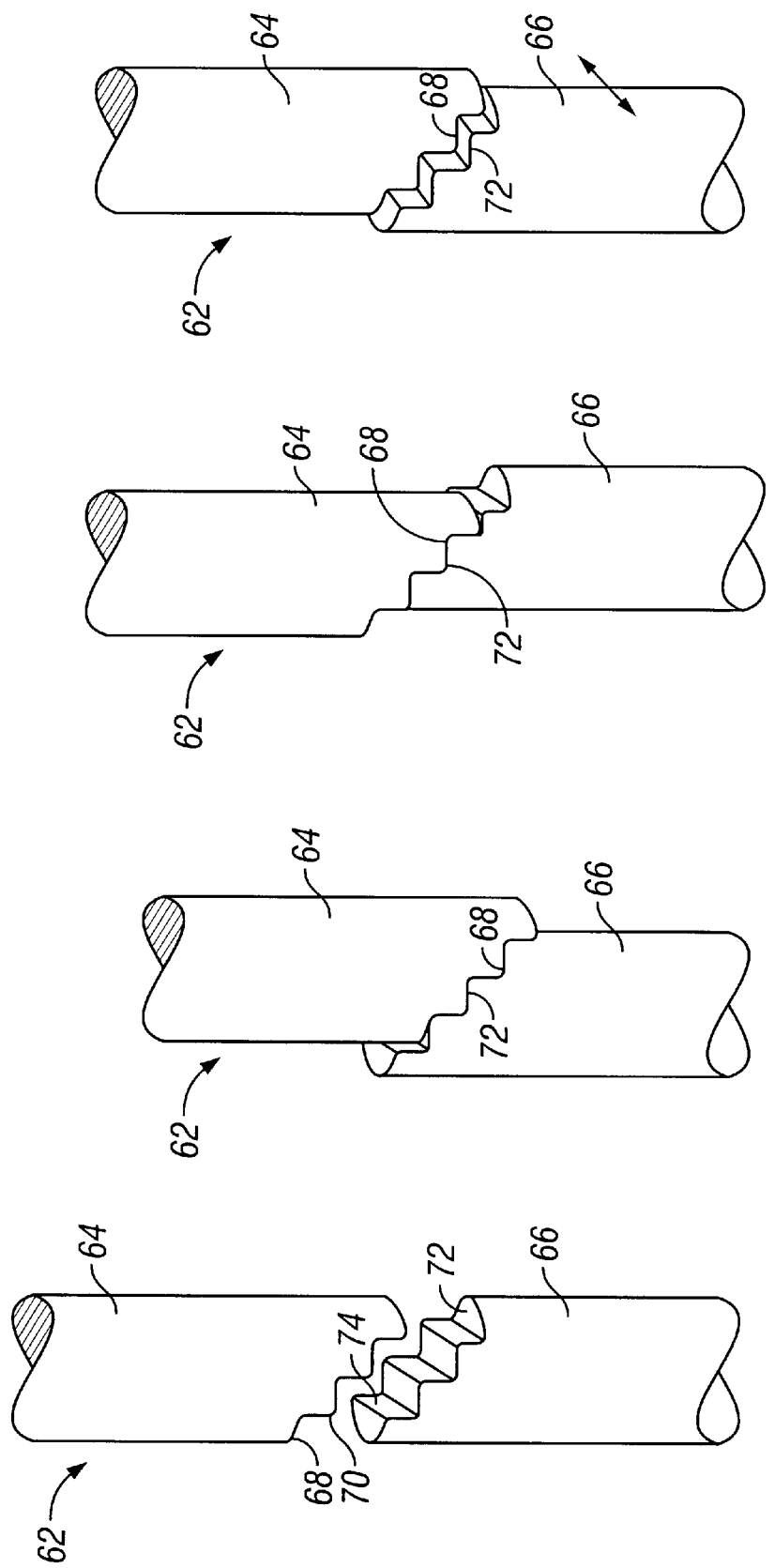

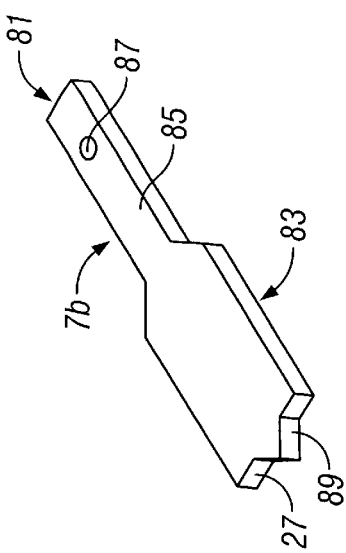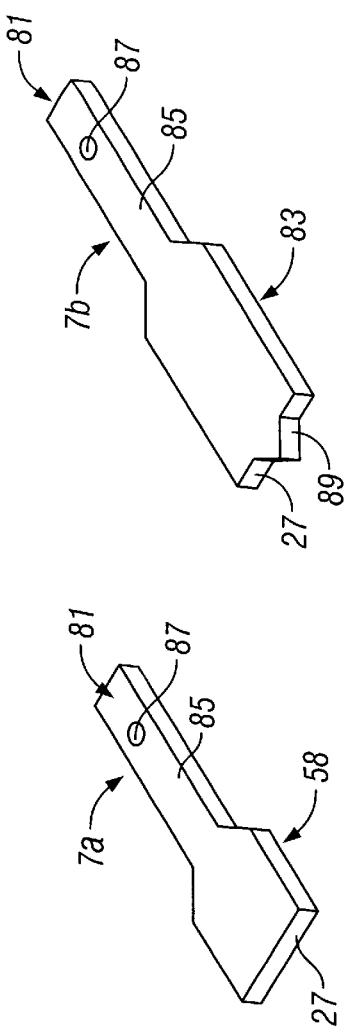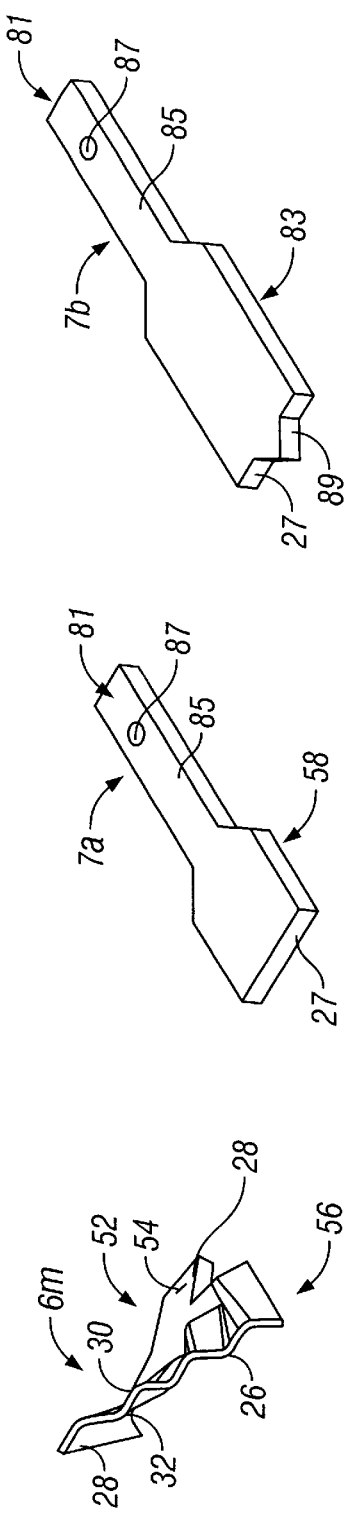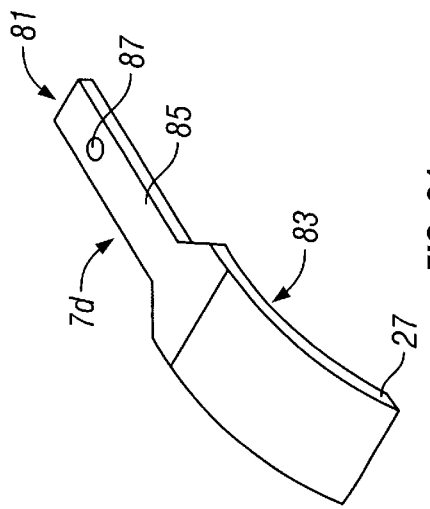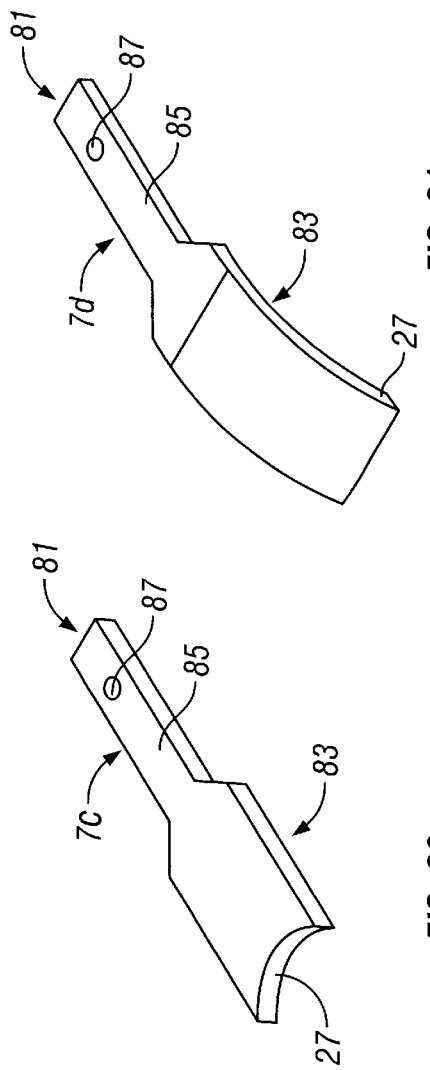

CORRUGATED OSTEOTOME BLADE AND METHOD OF SEVERING BONES AND OTHER ANATOMICAL STRUCTURES

CROSS-REFERENCE TO RELATED APPLICATIONS

This application claims priority from U.S. Provisional Patent Application Ser. No. 60/133,880, entitled "Osteotome and Method Utilizing a Corrugated Blade to Sever Bones" and filed May 12, 1999. The disclosure of that provisional application is incorporated herein by reference in its entirety.

BACKGROUND OF THE INVENTION

1. Technical Field

The present invention pertains to medical devices for severing bones and other anatomical structures (e.g., veins, arteries, soft tissue, bowels, etc.). In particular, the present invention pertains to medical devices that sever bones and other anatomical structures in a manner that facilitates correction of deformities and promotes healing.

2. Discussion of Related Art

Generally, bone deformities of patients may be corrected by various surgical procedures. These procedures may include severing a bone and subsequently manipulating the severed bone sections into a specific alignment, or cutting and/or removing particular sections of the bone. In order to sever or otherwise alter bone structure, the related art provides various medical instruments. For example, U.S. Pat. No. 4,586,496 (Keller) discloses a surgical chisel having a rigid shank and a thin elongated blade fixed at the shank front end. The shank and blade are displaceably guided in slideways of a chisel guide to provide the blade with buckling resistance.

U.S. Pat. No. 4,657,002 (Ray) discloses a bone impactor having a handle and a smooth shank. The shank tip includes a working surface that forms a symmetrical cylindrical concavity that may be fitted against a bone excrescence. The handle of the bone impactor is struck to compress the excrescence into the bone to relieve pressure on a nerve. U.S. Pat. No. 4,944,744 (Ray) further discloses the bone impactor working surface to include a linear knurl.

U.S. Pat. Nos. 4,150,675 (Comparetto), 4,349,058 (Comparetto) and 4,728,330 (Comparetto) disclose an osteotome including an arcuate blade portion and a planar cutting blade integrally secured thereto. The arcuate blade portion is axially elongated relative to the planar blade to permit the arcuate blade portion to remain in an initially cut bone section while the osteotome is rotated to perform a second cut. The two cuttings serve to remove a section of bone, thereby facilitating precise alignment of bone sections after repositioning to correct an original bone deformity. A blunt instrument is brought down upon the head end of the osteotome to sever the bone. The planar cutting blade may alternatively have a jagged or sinusoidal (e.g., French, curve type) configuration.

U.S. Pat. Nos. 4,952,214 (Comparetto) and 5,035,698 (Comparetto) disclose an arcuate osteotomy blade having a shaft disposed parallel to its cutting edge to enhance blade strength and control of the cut. The shaft is gripped by a linearly reciprocating saw, while blade teeth are formed along a leading edge parallel to the blade curvature.

U.S. Pat. No. 4,708,133 (Comparetto) discloses a bone cutter including a curved blade and an adjustable radial arm for making arcuate cuts with the use of a reciprocating saber or jig saw. The blade includes a curved body and double blade edges to effect left and right curved cuts in bone, and preferably includes saw teeth on only one of the blade edges. The curved body enhances blade strength by resisting flexure and buckling.

U.S. Pat. No. 5,147,364 (Comparetto) discloses an apparatus for performing arcuate osteotomies wherein a wedge-shaped correction is filed rather than sawed from the bone. A combined saw and file has a curved blade with teeth along a longitudinal edge for making an arcuate cut in a direction perpendicular to the edge, and file teeth on one or both of the curved surfaces for filing out the correction. The blade is engaged by a motor drive that reciprocates the blade to saw and file the bone.

The related art suffers from several disadvantages. In particular, the Keller chisel produces relatively flat severed bone surfaces from a cut, thereby requiring significant stabilization techniques (e.g., screws, pins, wires, etc.) to maintain the severed bone sections in position to correct a deformity. Further, the flat surfaces limit the surface area of contacting bone sections and, therefore, restrict the bone healing potential. The Ray devices are specifically configured to compress, rather than cut, a bone excrescence. As such, the Ray devices have limited applicability and cannot be utilized for severing and repositioning bones to correct deformities.

The Comparetto osteotome does facilitate severing and repositioning of bone to correct deformities, but is driven manually and typically requires extensive effort on the part of a surgeon to sever a bone. Further, the arcuate blade portion of the osteotome produces severed bone surfaces that are flat and smooth, thereby limiting the surface areas of the severed bone sections and restricting the bone healing potential. Although the osteotome planar blade may include a jagged configuration, this portion occupies a relatively minute section of the osteotome and only marginally increases the surface area of the severed bone sections and healing potential. Moreover, in order to correct bone deformities with the Comparetto osteotome, several cuts are formed in the bone to remove a bone section, while the severed sections are manipulated into a position to correct the deformity. This process necessitates accurate determinations with respect to the angle of the cuts and dimensions of the removed bone section, thereby complicating the procedure and increasing the risk of error and injury to a patient.

The Comparetto blades may be utilized to similarly correct bone deformities by requiring several cuts to be formed in the bone to remove a bone section. However, this complicates the procedure and increases the risk of error and injury to a patient as described above. Further, the blades produce severed bone surfaces that are flat and smooth, thereby limiting the surface areas of the severed bone sections and restricting healing potential as described above. Although the Comparetto file provides for a single cut to correct a deformity, the severed bone surfaces are flat and smooth, while the file width and corresponding correction must be carefully determined. Thus, the file limits the severed bone surface area and healing potential, and further complicates the procedure while increasing the risk of error and injury to a patient. In addition, the aforementioned related art does not provide manners or instruments for performing similar corrective procedures on other anatomical structures (e.g., veins, arteries, soft tissue, bowels, etc.).

The above and still further objects, features and advantages of the present invention will become apparent upon consideration of the following detailed description of spe-

OBJECTS AND SUMMARY OF THE INVENTION

Accordingly, it is an object of the present invention to sever bones or other anatomical structures (e.g., veins, arteries, soft tissue, bowels, etc.) via a corrugated blade to facilitate repositioning of the severed sections in a mated fashion to enhance stability and promote healing.

It is another object of the present invention to produce various corrugated patterns in severed bone sections to facilitate repositioning of the bone sections in various manners to correct bone deformities.

Yet another object of the present invention is to increase surface area in severed bone sections or other anatomical structures to promote healing of the structure when the severed sections are reunited.

Still another object of the present invention is to enhance stability in severed bone sections, thereby reducing the amount of fixation devices required to maintain the bone sections in a desired position to correct a deformity.

A further object of the present invention is to adapt a corrugated blade for use with a power saw to sever bones or other anatomical structures in a manner that facilitates repositioning of the bones in a mated fashion.

The aforesaid objects are achieved individually and/or in combination, and it is not intended that the present invention be construed as requiring two or more of the objects to be combined unless expressly required by the claims attached hereto.

According to the present invention, a corrugated blade is utilized to form corrugated patterns in ends of a severed bone. The corrugated patterns enable the severed bone sections to be coupled in a mated fashion, thereby providing increased contact area between the bone sections and enhanced stability to promote healing. Further, the corrugated patterns may be offset when coupling the severed bone sections together in order to adjust the bone length and/or orientation to correct a deformity.

The corrugated blade may have varying dimensions to accommodate different sized bones, and may be configured in various fashions (e.g., left or right curve, curved upward or downward, arcuate, etc.) to facilitate manipulation of severed sections into a desired position or orientation. The corrugated blade may be attached to an osteotome handle for manual use, or may be adapted to engage a power tool or saw to sever the bone. Further, the corrugated blades may be utilized for other anatomical structures (e.g., veins, arteries, soft tissue, bowels, etc.) to provide a mated fit between severed sections and promote healing as described above.

The corrugated blade may further be configured in the form of a bone staple. The staple is inserted into bone sections to enhance the connection between those sections. The staple includes perforations to permit the staple to remain within the bone, and various openings to permit the bone to grow through the holes to reinforce the connection.

The corrugated blades of the present invention provides several advantages and may be utilized for various surgical procedures. In particular, the corrugated blades are preferably implemented by razor sharp micro thin surgical blades (e.g., generally less than one millimeter) to sever bone or other anatomical structures, and increase the healing area of the severed bones by at least eight percent. The corrugated blades provide ease of use and simplistic action (e.g., one anatomical plane), while providing a stable osteotomy, thereby reducing or eliminating use of fixation devices (e.g., screws, plates, rods, staples, etc.). In fact, only a single Kirschner wire or single screw fixation is typically required. The corrugated blades may be utilized in a doctor's office, hospital or other medical facility and may be attached to an osteotome handle for hand held operation via a mallet (e.g., when no power is available), or adapted for use with power reciprocating saws (e.g., Zimmer/Hall, Stryker or other conventional models).

The corrugated blades sever bone without burning or producing bone chips or residue, thereby eliminating the need to flush the bone. The corrugated blades may be utilized wherever oscillating or sagital saws or osteotomies are employed. Procedures for which the corrugated blades may be utilized include: arthrodesis of bones and joints in humans and animals; bone fracture repairs in humans and animals; soft tissue repair in tendons, ligaments, joint capsules and muscles in humans and animals; surgical anastamosis (e.g., uniting) of arteries and veins in humans and animals; and fixation of fractures and arthodesis in humans and animals via the staple.

BRIEF DESCRIPTION OF THE DRAWINGS

FIG. 5 is a view in perspective and partial section of the bone of FIG. 4 severed by the osteotome of FIG. 1.

FIG. 6 is a view in perspective and partial section of the severed bone of FIG. 5 manipulated to decrease the bone length to correct a deformity according to the present invention.

FIG. 7 is a view in perspective and partial section of the severed bone of FIG. 5 manipulated to increase the bone length to correct a deformity according to the present invention.

FIG. 8 is a view in perspective and partial section of the severed bone sections of FIG. 5 manipulated in fore and/or aft directions to correct a deformity according to the present invention.

FIG. 27 is a view in perspective of a helical corrugated blade for use with a power saw according to the present invention.

FIG. 28 is a view in perspective of a planar blade adapted for use with a power saw according to the present invention.

FIG. 29 is a view in perspective of a planar blade for use with a power saw and having a pointed tip according to the present invention.

FIG. 30 is a view in perspective of a planar blade for use with a power saw and having a tapered or recessed distal end according to the present invention.

FIG. 31 is a view in perspective of a planar blade for use with a power saw having a longitudinally curved blade portion according to the present invention.

DETAILED DESCRIPTION OF THE PREFERRED EMBODIMENTS

Figure 1:
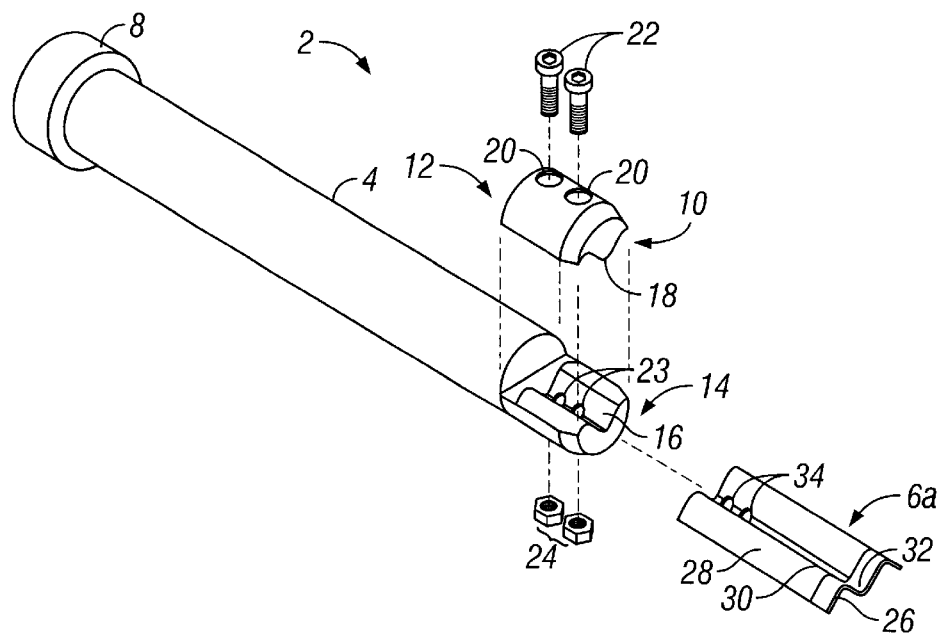
FIG. 1 is an exploded view in perspective of an osteotome employing a corrugated blade according to the present invention.

An osteotome employing a corrugated blade according to the present invention is illustrated in FIG. 1. Specifically, an osteotome 2 includes a handle 4 and a blade 6a disposed at the handle distal end. Handle 4 is substantially cylindrical and includes a head 8 and a blade attachment member 10. Head 8 is substantially cylindrical and is disposed at the handle proximal end. The head has cross-sectional transverse dimensions greater than those of handle 4 and is typically struck by a blunt object, such as a mallet, to drive blade 6a through a bone or other anatomical structure as described below. The blade attachment member is disposed at a handle distal end and includes a removable upper section 12 and a lower section 14. The upper and lower sections are each generally semi-cylindrical having a slightly tapered distal end. The lower section is formed integral with and extends from the handle distal end and includes a substantially central recess 16 defined therein. Upper section 12 includes a substantially central peak or bump 18 defined therein and has dimensions similar to lower section 14. The recess and peak are configured for mated engagement with blade 6a to secure the blade to the handle. In particular, upper section 12 further includes a pair of openings 20 defined in its top surface for receiving nuts 22, while lower section 14 includes a pair of openings 23 defined in its bottom surface in substantial alignment with openings 20 for accommodating bolts 24. The nuts and bolts secure the blade in blade attachment member 10 between the upper and lower sections as described below. The bolts each preferably include a head configured to be manipulable by an Allen type wrench. Alternatively, the blade may be formed integral with handle 4 (e.g., insert molded). Handle 4 is typically constructed of plastic and has a length of approximately fifteen centimeters, but may be constructed of any suitable materials and may be of any shape or size. Moreover, the upper and lower sections may be configured in any manner providing suitable engagement with any blade configuration.

Blade 6a has a generally rectangular periphery and is preferably constructed of stainless steel to produce a sharp cutting instrument or blade. The blade may be manufactured from flat rolled material, wire, round material, bar type material or any other suitable materials, and may have any peripheral shape. Blade 6a may be disposable after a single use, or autoclaved (e.g., sterilized) for re-use in additional medical procedures, and may be available in a sterile or non-sterile condition. A distal or cutting edge 26 of blade 6a extends along the shorter blade dimension and is generally in the form of a sawtooth wave. The blade includes a plurality of successive blade sections 28, each substantially rectangular and extending between the blade proximal and distal edges. The blade sections are arranged to alternately define peaks 30 and a valley 32 between adjacent blade sections, thereby forming the corrugated blade configuration. The corrugated blade configuration typically includes rounded peaks and valleys, however, the peaks and valleys may be formed with any type of rounded, squared or angled configuration. Successive blade sections 28 are preferably interconnected at an angle of approximately 90°. However, the blade sections may be interconnected at any desired angle in the approximate range of 1°–179°, with angles in the approximate range of 70°–110° being the most practical. Further, adjacent blade sections may be interconnected at the same or different angles throughout the blade configuration. For example: a first pair of adjacent blade sections may be interconnected at an angle of 90°, while a second pair of adjacent blade sections may be interconnected at an angle of 105°; or valley 32 may have a different angle than each peak 30. Moreover, the corrugated blade configuration may include any corrugation frequency (e.g., any quantity of peaks and valleys in a given area) or combinations of corrugation frequencies, and any quantity of peaks and valleys. A pair of openings 34 are substantially centrally defined in valley 32 toward the blade proximal edge and receive nuts 22 to secure the blade to handle 4 in a stable fashion as described below. By way of example only, blade 6a includes two peaks and one valley and has a longer blade dimension or length of approximately five centimeters and a shorter or transverse blade dimension of approximately sixteen millimeters; however, the blade may be of any size or shape to accommodate various body portions.

Blade 6a is typically secured to handle 4 via nuts 22 and bolts 24. Specifically, the proximal end of blade 6a is inserted within blade attachment member 10 with the blade distal or cutting edge extending distally of the handle. The blade attachment member lower section receives valley 32 within recess 16, while upper section peak 18 is disposed in that valley. The blade is thus positioned within the blade member between the upper and lower sections such that blade openings 34 are aligned with the openings defined in the upper and lower sections. Nuts 22 are inserted through aligned openings 20, 23 and 34, while bolts 24 engage the nuts and apply force to secure the blade between the upper and lower sections. The handle may include any quantity or type of fastening devices to secure the blade to the handle.

Figure 2A:
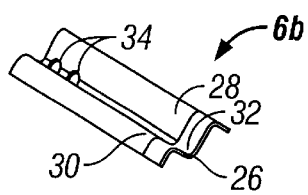
FIG. 2A is a view in perspective of an alternative corrugated blade for the osteotome of FIG. 1 according to the present invention.
Figure 2B:
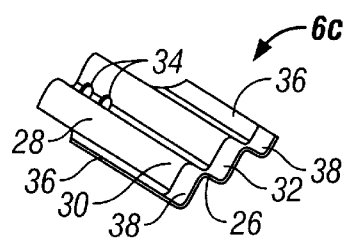
FIG. 2B is a view in perspective of yet another corrugated blade for the osteotome of FIG. 1 according to the present invention.
Figure 2C:
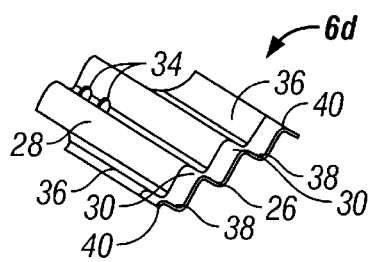
FIG. 2C is a view in perspective of still another corrugated blade for the osteotome of FIG. 1 according to the present invention.

Alternative corrugated blade configurations for osteotome 2 are illustrated in FIGS. 2A–2C. Specifically, blade 6b (FIG. 2A) is substantially similar to blade 6a described above, except that blade 6b has transverse dimensions slightly less than those of blade 6a. Blade 6b, by way of example, has a transverse dimension of approximately twelve millimeters, and is typically employed to sever bones having lesser cross-sectional dimensions than those severed by blade 6a.

In order to sever bones of greater cross-sectional dimensions, the blade dimensions may be increased to accommodate the larger bones. Referring to FIG. 2B, blade 6c is substantially similar to blades 6a, 6b described above except that blade 6c has greater transverse dimensions and includes additional blade sections 36. By way of example only, blade 6c has a transverse dimension of approximately twenty millimeters. Blade sections 36 are substantially similar to and transversely extend from blade sections 28 to form an additional valley 38 toward each of the blade transverse edges. The length of sections 36 are slightly less than those of sections 28 with sections 36 extending between distal edge 26 and a distal one of openings 34. This configuration enhances stability of the blade during use.

FIG. 2C illustrates yet another corrugated blade. Specifically, blade 6d is substantially similar to blade 6c described above, except that blade 6d has greater transverse dimensions and includes additional blade sections 36. By way of example only, blade 6d has a transverse dimension of approximately twenty-five millimeters. Blade sections 36 essentially form an additional peak 40 toward each of the blade transverse edges and adjacent a corresponding valley 38. Sections 36 extend between distal edge 26 and a distal one of openings 34 as described above to enhance stability of the blade during use.

Figure 3A:
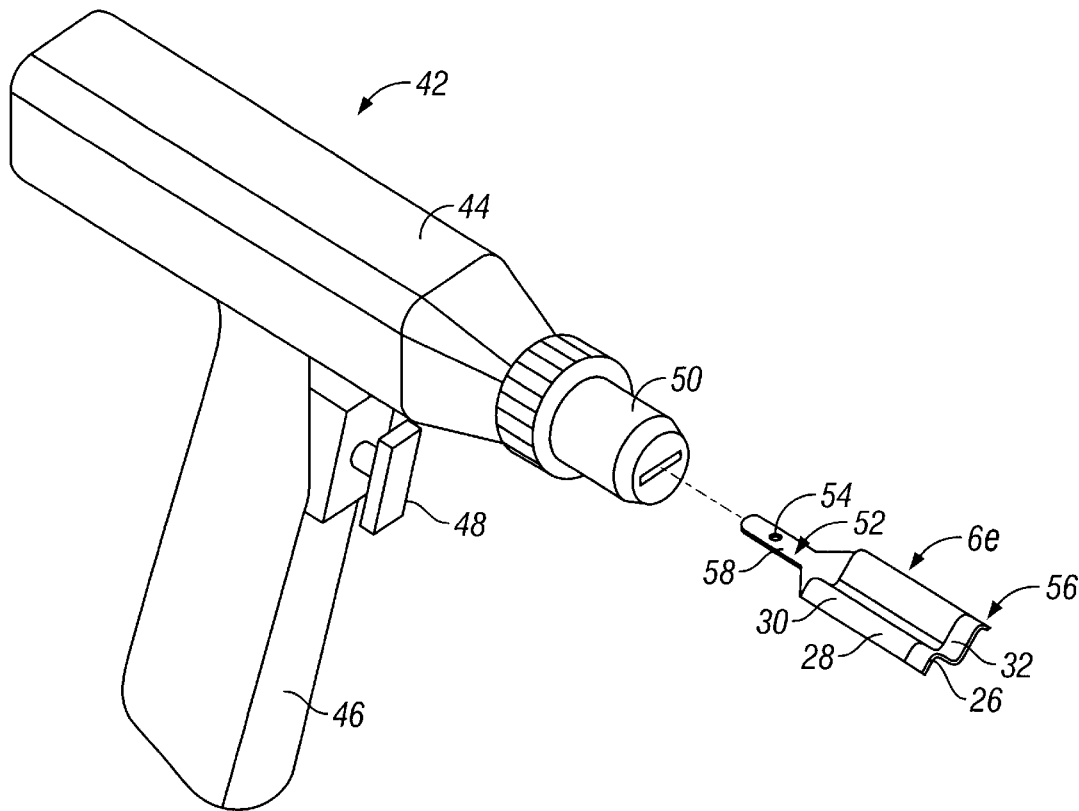
FIG. 3A is an exploded view in perspective of a corrugated blade for use with a power reciprocating saw according to the present invention.

The corrugated blades may be utilized with osteotome 2 for manual operation, or may be adapted for use with a reciprocating power saw as illustrated in FIG. 3A. Specifically, a power saw 42 includes a body 44, a handle 46 and a trigger 48. A blade member 50 is disposed at a distal end of the body for engaging a blade. Handle 46 is attached to a substantially central portion of the body underside and includes trigger 48 for saw actuation. The saw may be implemented by any conventional power saws, but, by way of example only, is implemented by a Hall/Zimmer recip-rocator saw, model 5071-004.

A corrugated blade 6e for use with saw 42 is substantially similar to blade 6b described above, except that blade 6e is configured for attachment to the saw. Specifically, blade 6e has a generally rectangular corrugated blade portion 56 and an adapter 52 attached to the blade portion proximal end. Distal or cutting edge 26 of blade 6e extends along the shorter blade dimension and is generally in the form of a sawtooth wave. Blade 6e includes a plurality of successive blade sections 28, each substantially rectangular and extending between the blade distal edge and adapter 52. The blade sections are arranged to alternatively define peaks 30 and a valley 32 between adjacent blade sections as described above. Adapter 52 extends from the blade portion proximal end and tapers to form an elongated substantially rectangular bar 58 at its distal portion. An opening 54 is defined in bar 58 toward the bar proximal end to facilitate engagement of blade 6e by blade member 50 of saw 42. Blade member 50 includes an engagement mechanism to removably secure the blade to the saw.

Figure 3B:
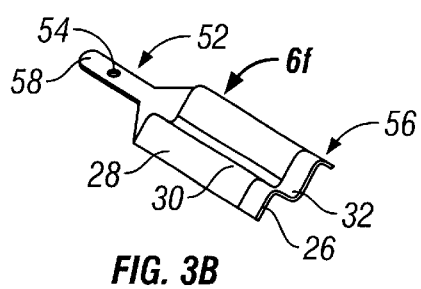
FIG. 3B is a view in perspective of an alternative corrugated blade for the saw of FIG. 3A according to the present invention.

An alternative corrugated blade for use with power saw 42 is illustrated in FIG. 3B. Specifically, blade 6f is substantially similar to blade 6e described above, except that blade 6f has transverse blade portion dimensions greater than those of blade 6e. By way of example only, blade 6e has a length of approximately seven centimeters and a transverse blade portion dimension of approximately twelve millimeters, while blade 6f has a substantially similar length with a transverse blade portion dimension of approximately sixteen millimeters. The lesser blade portion dimension enables blade 6e to be employed for severing smaller bones. Blade 6f includes adapter 52 as described above to facilitate engagement by power saw 42. The adapter is attached to and extends from the proximal end of blade portion 56.

Figure 3C:
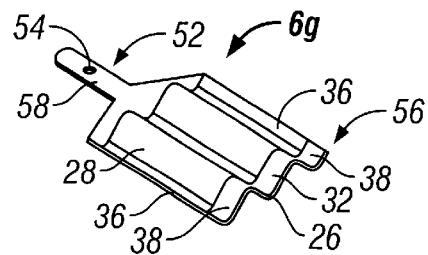
FIG. 3C is a view in perspective of yet another corrugated blade for the saw of FIG. 3A according to the present invention.

In order to sever bones of greater cross-sectional dimensions, the blade portion dimensions may be increased as illustrated in FIG. 3C. Specifically, blade 6g is substantially similar to blade 6f described above, except that blade 6g has a transverse blade portion dimension slightly greater than that of blade 6f and includes additional blade sections 36 as described above for blade 6c. By way of example only, blade 6g has a transverse blade portion dimension of approximately twenty millimeters. Blade sections 36 extend from blade sections 28 to form an additional valley 38 toward each of the blade portion transverse edges. Blade 6g further includes adapter 52 as described above to facilitate engagement by power saw 42. The adapter is attached to and extends from the proximal end of blade portion 56.

Figure 4:
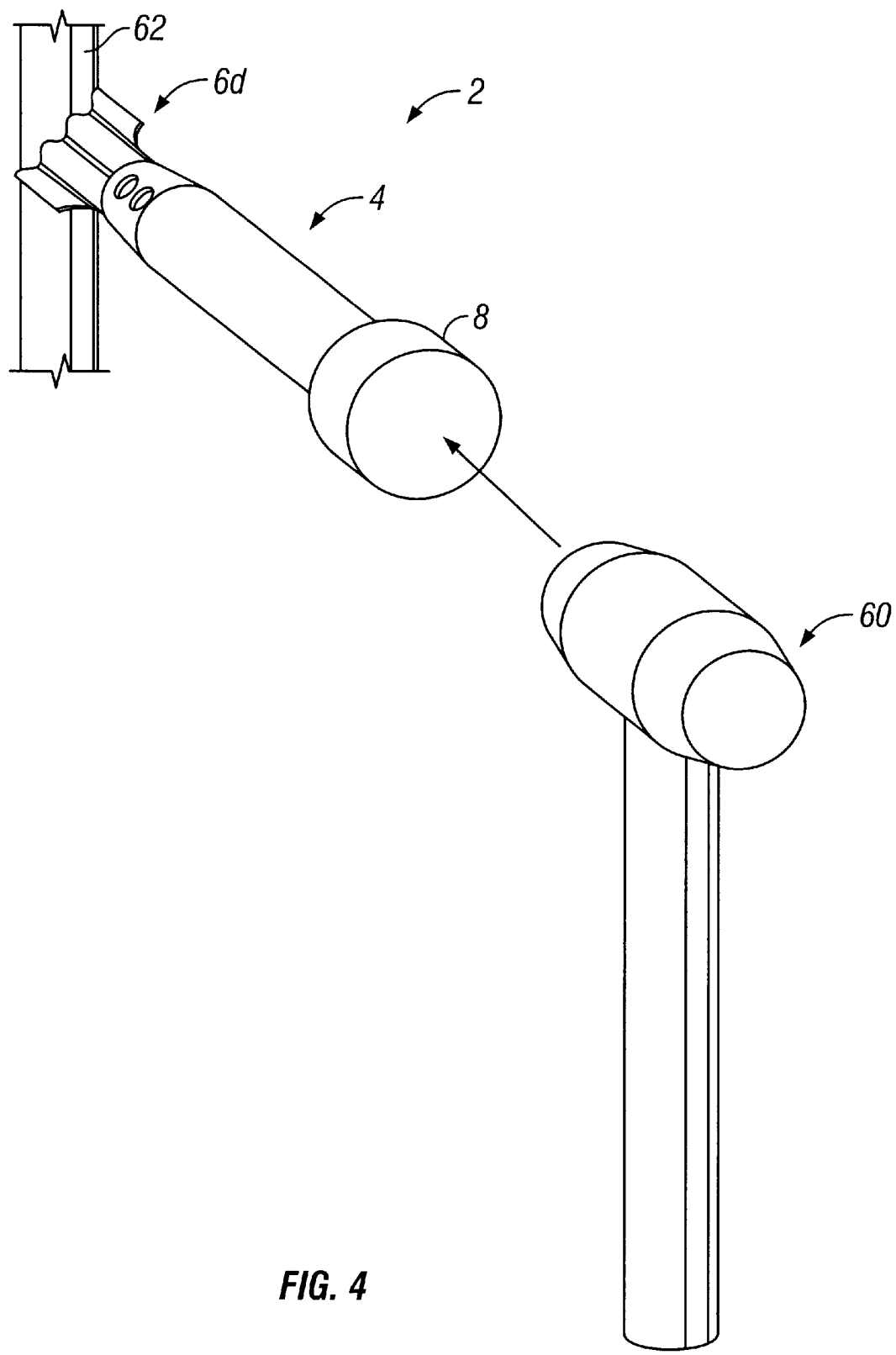
FIG. 4 is an exploded view in perspective of the osteotome of FIG. 1 severing a bone at an angle relative to the bone surface.
Figure 9:
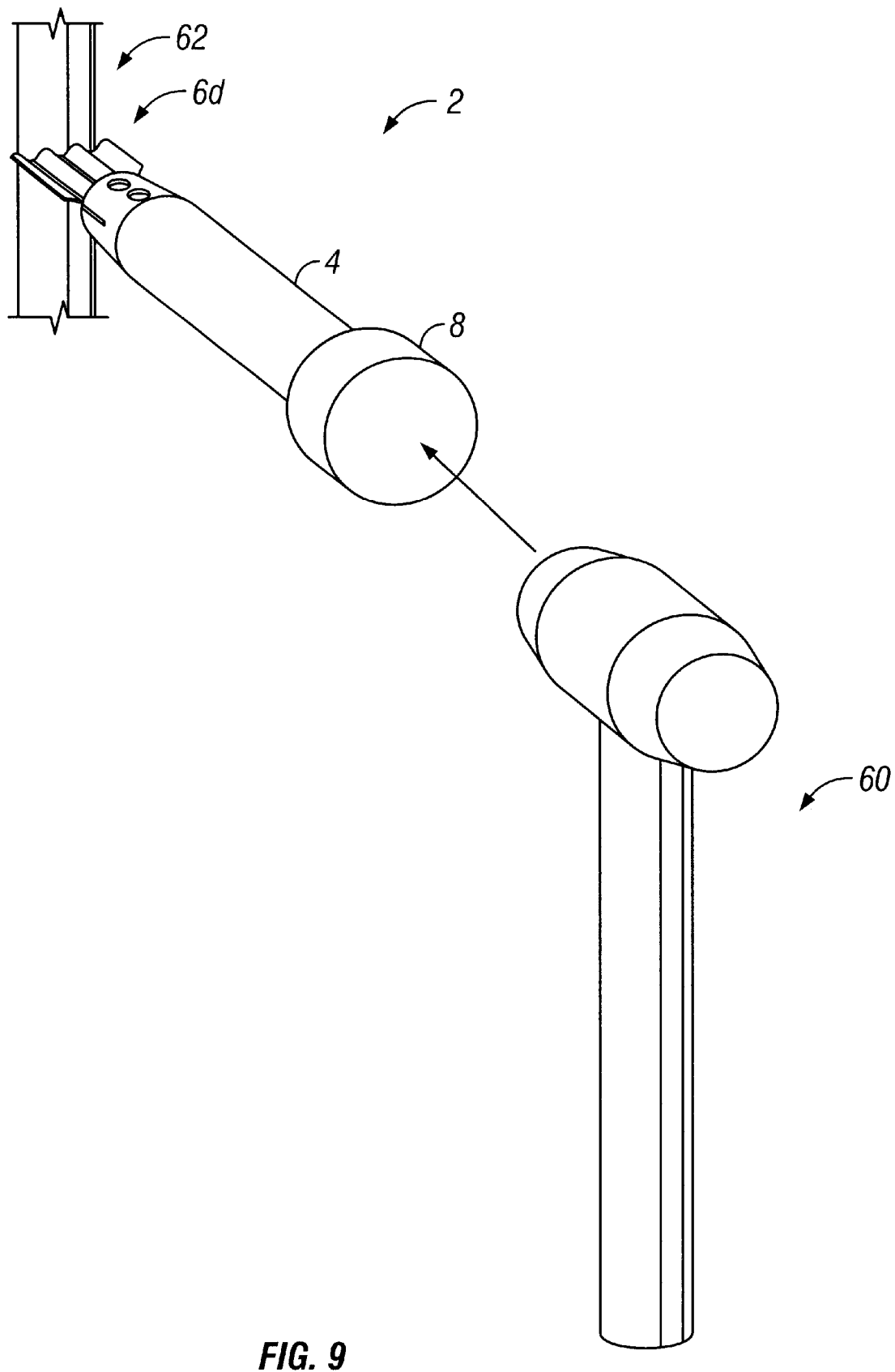
FIG. 9 is a view in perspective of the osteotome of FIG. 1 severing a bone with the blade oriented substantially parallel with the bone transverse axis.

Operation of osteotome 2 (FIG. 1) with a corrugated blade is described with reference to FIGS. 4–5. Generally, the corrugated blades of the present invention are utilized to sever bones in order to correct bone deformities or to reset bones to promote healing. The corrugated blades may be utilized with an osteotome and a conventional mallet 60, or may be engaged by a power tool or saw as described above. By way of example only, bone severance is illustrated utilizing blade 6d in conjunction with osteotome 2 and a mallet, however, other blade configurations and/or a power tool may be utilized in a similar manner. Specifically, blade 6d is positioned proximate a bone 62 and oriented at a desired angle relative to the bone surface. Lower angles of osteotome orientation (e.g., lower than 20°) are generally utilized for resetting bones, while increased orientation angles (e.g., greater than 20°) are typically utilized for adjusting bone lengths as described below. By way of example only, the osteotome is oriented at an approximate 45° angle relative to a bone transverse axis to enable adjustment of bone length as described below for FIGS. 6–7. Mallet 60 is manipulated to strike head 8 at the handle proximal end, thereby causing blade 6d to penetrate and sever bone 62 into bone sections 64, 66 (FIG. 5). Bone section 64 includes a bottom surface 68 having a series of successive steps 70 defined therein during bone severance by the configuration of blade 6d. Each step 70 is defined at a successive distance from a proximal end of bone section 64 due to the orientation angle of blade 6d during bone severance. In other words, the distance between a successive step 70 and the proximal end of bone section 64 successively increases (e.g. from left to right as viewed in FIG. 5) with each step. Similarly, bone section 66 includes a top surface 72 in facing relation with bottom surface 68 and having a series of successive steps 74 defined therein during bone severance by the configuration of blade 6d. Each step 74 is defined at a successive distance from a distal end of bone section 66 due to the orientation angle of blade 6d during bone severance as described above. The distance between a successive step 74 and the distal end of bone section 66 successively decreases (e.g. from left to right as viewed in FIG. 5) with each step. Steps 70, 74 are configured to interleave such that bone sections 64, 66 may be coupled in a mated fashion for healing. The step configurations of the severed bone sections essentially provide increased surface area or, in other words, a greater area of contact between the bone sections to promote healing. Further, the step configurations prevent slippage between and provide sturdier support for the coupled bone sections during healing.

The osteotome may utilize the alternative blade configurations of blades 6a, 6b and 6c to sever a bone and promote healing in substantially the same manner described above for blade 6d, except that the facing surfaces of the severed bone sections include configurations defined therein during bone severance corresponding to the particular blade utilized.

The corrugated blade configurations described above may further provide for modification of bone structure as illustrated in FIGS. 6–8. By way of example only, bone 62 (FIG. 4) is initially severed by osteotome 2 having blade 6d and oriented at an approximate 45° angle as described above. The osteotome severs the bone into bone sections 64, 66 and defines mated step configurations within respective bone section 68, 72 surfaces as described above. The severed bone sections are manipulated such that the step pattern of bone section 64 is shifted to the right or in a downward direction (e.g., as viewed in FIG. 6) relative to the step pattern of bone section 66 by a quantity of steps (e.g., at least one) to reduce the length of bone 62. Either or both bone sections 64, 66 may be manipulated relative to each other to achieve this result.

Conversely, the step pattern of bone section 64 may be shifted to the left or in an upward direction (e.g., as viewed in FIG. 7) relative to the step pattern of bone section 66 by a quantity of steps (e.g., at least one) to increase the length of bone 62. Either or both bone sections 64, 66 may be manipulated relative to each other to achieve this result. Alternatively, the osteotome may utilize the corrugated blade configurations of blades 6a, 6b and 6c to sever the bone for modification of bone structure in substantially the same manner described above for blade 6d.

As another procedural alternative, bone section 64 may be moved medially or transversely (i.e., into or out from the plane of the drawing) relative to section 66 (e.g., as indicated by the double arrow in FIG. 8). In any case, the sawtooth or peak-valley cuts that extend across mating surfaces of bone sections 64, 66 permit those sections to be stably positioned during the knitting or healing process at the bone section interface. The sawtooth cuts also increase the surface area of the mated bone section surfaces, as compared to planar mated surfaces, so that a stronger bond is obtained and the healing time is reduced.

A further modification of bone structure is illustrated in FIGS. 9–13. By way of example only, bone 62 (FIG. 9) is initially severed by osteotome 2 having blade 6d and oriented with the cutting edge substantially parallel to the bone transverse axis. The osteotome severs the bone into bone sections 64, 66 as described above and defines mated corrugated configurations within respective bone section surfaces 68, 72 (FIG. 10) corresponding to the configuration of the blade. The severed bone sections are manipulated such that the corrugated pattern of bone section 64 is shifted to the left (e.g., as viewed in FIG. 11) relative to the pattern of bone section 66 by a desired offset to reposition bone 62 to correct a deformity. Either or both bone sections 64, 66 may be manipulated relative to each other to achieve this result.

Conversely, the corrugated pattern of bone section 64 may be shifted to the right (e.g., as viewed in FIG. 12) relative to the pattern of bone section 66 by a desired offset to reposition bone 62 to correct a deformity. Either or both bone sections 64, 66 may be manipulated relative to each other to achieve this result. Alternatively, the osteotome may utilize the corrugated blade configurations of blades 6a, 6b and 6c to sever the bone for modification of bone structure in substantially the same manner described above for blade 6d.

Figure 13:
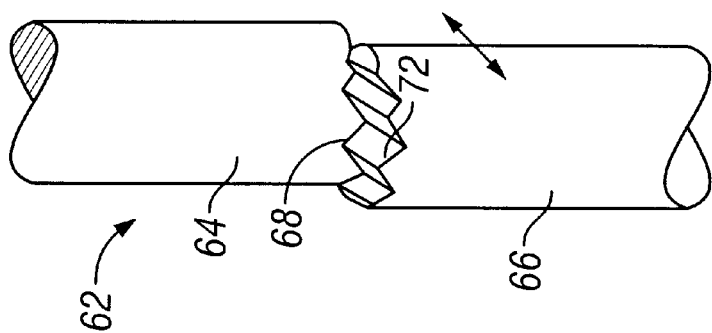
FIG. 13 is a view in perspective and partial section of the severed bone sections of FIG. 10 manipulated in fore and/or aft directions to correct a deformity according to the present invention.
Figure 12:
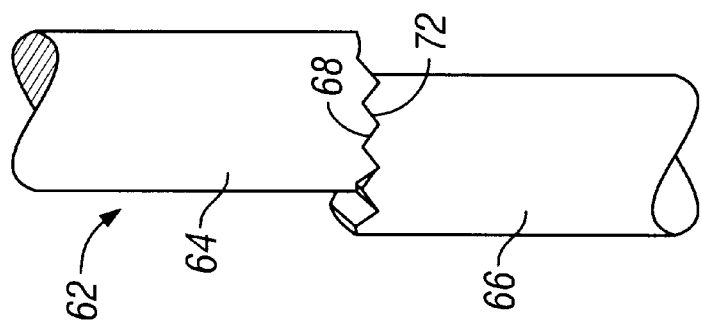
FIGS. 11–12 are views in perspective and partial section of the severed bone sections of FIG. 10 manipulated transversely to correct a deformity according to the present invention.
Figure 11:
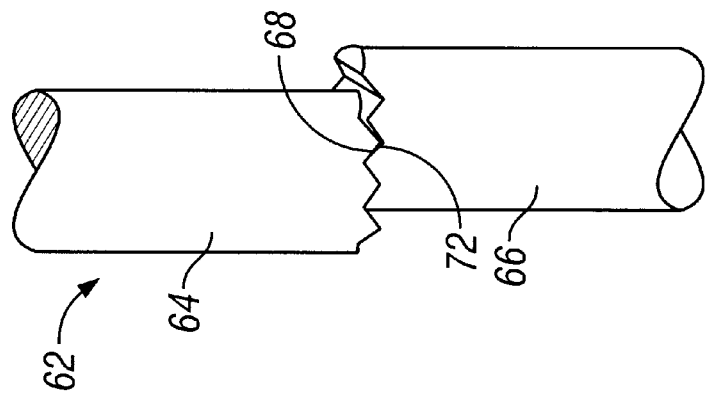
Figure 10:
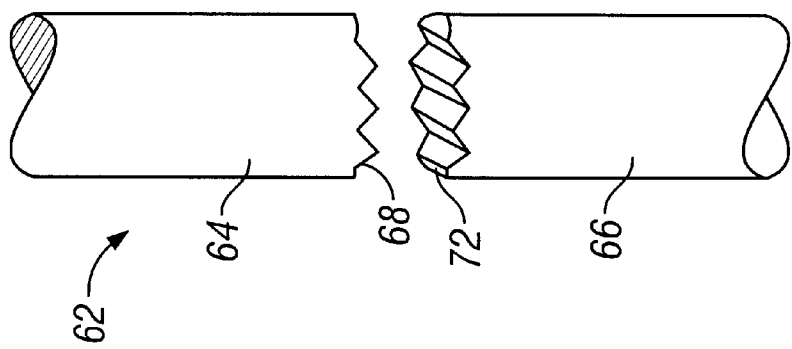
FIG. 10 is a view in perspective and partial section of the bone of FIG. 9 severed by the osteotome of FIG. 1.

As another alternative, bone section 64 may be moved medially or transversely (i.e., into or out from the plane of the drawing) relative to section 66 (e.g., as indicated by the double arrow in FIG. 13). In any case, the sawtooth or peak-valley cuts that extend across the mating surfaces of bone sections 64, 66 permit those sections to be stably positioned during the knitting or healing process at the bone section interface as described above. The sawtooth cuts also increase the surface area of the mated bone section surfaces, as compared to planar mated surfaces, so that a stronger bond is obtained and the healing time is reduced.

Figure 14:
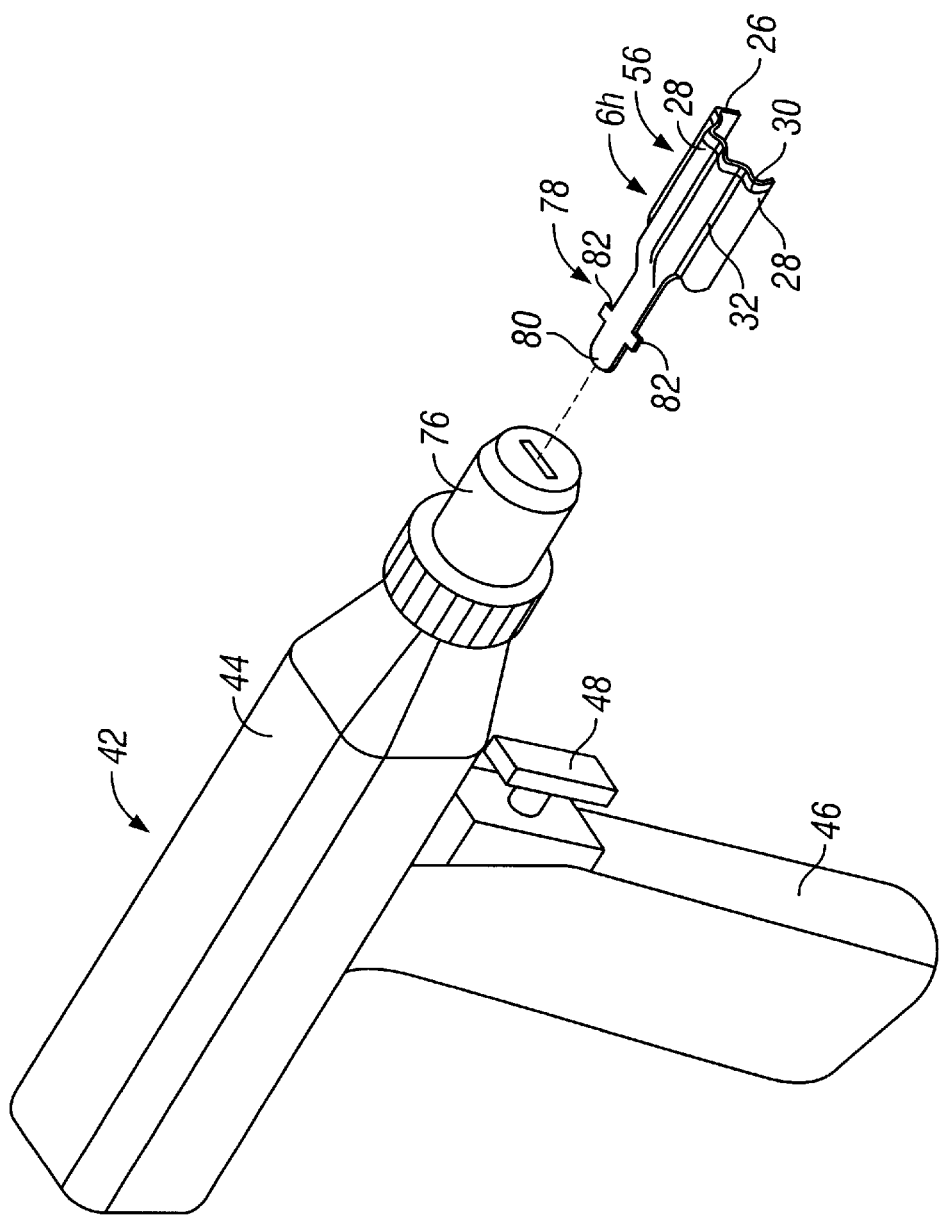
FIG. 14 is an exploded view in perspective of an arcuate corrugated blade employed by a power reciprocating saw according to the present invention.
Figure 15:
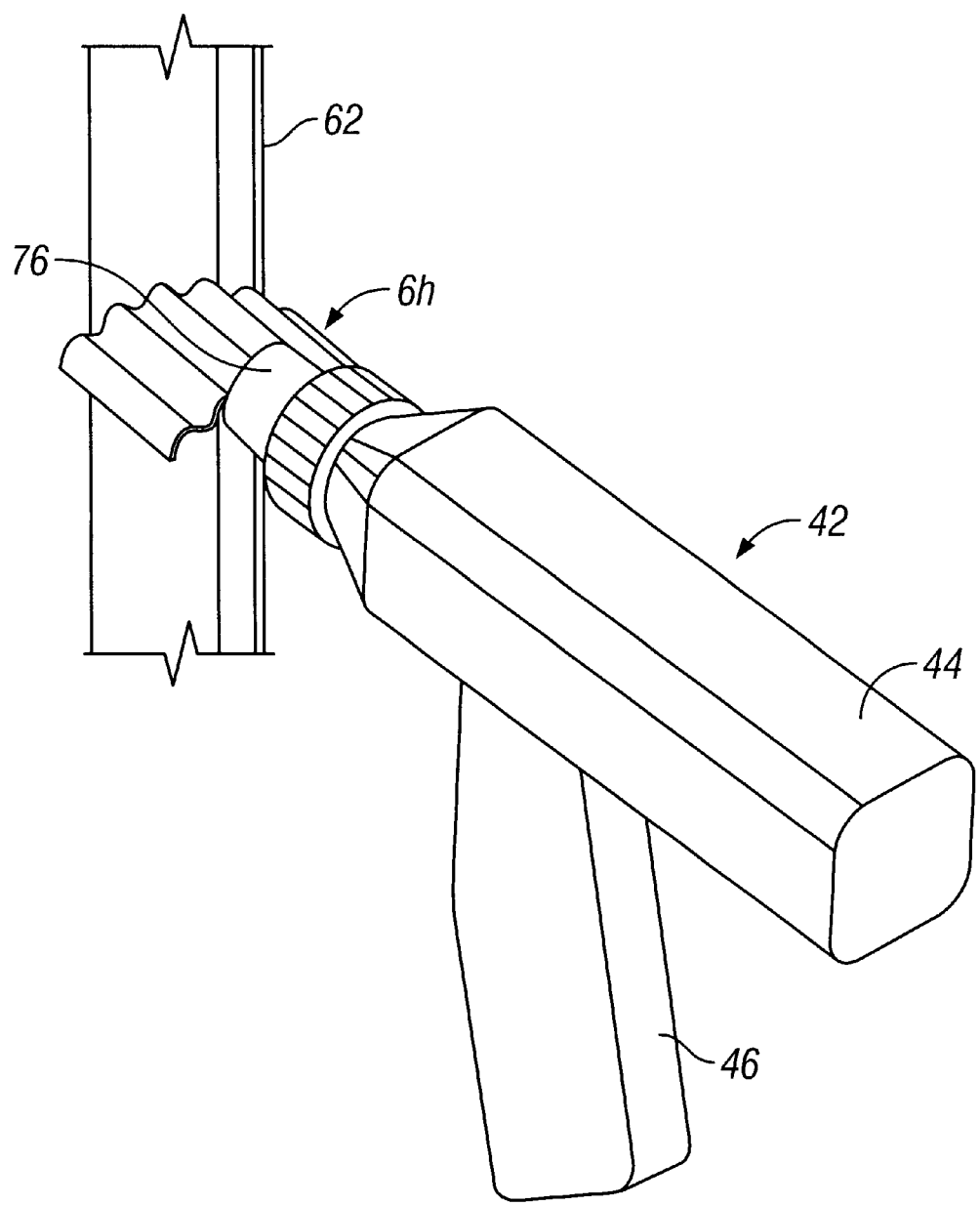
FIG. 15 is a view in perspective of the power saw of FIG. 14 severing a bone with the arcuate corrugated blade.
Figure 19:
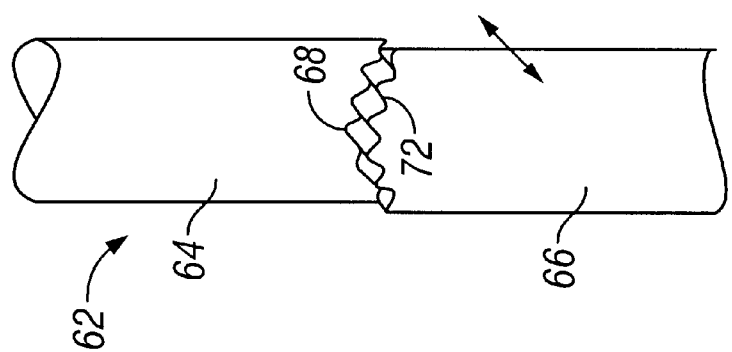
FIG. 19 is a view in perspective and partial section of the severed bone sections of FIG. 16 manipulated in fore and/or aft directions to correct a deformity according to the present invention.
Figure 18:
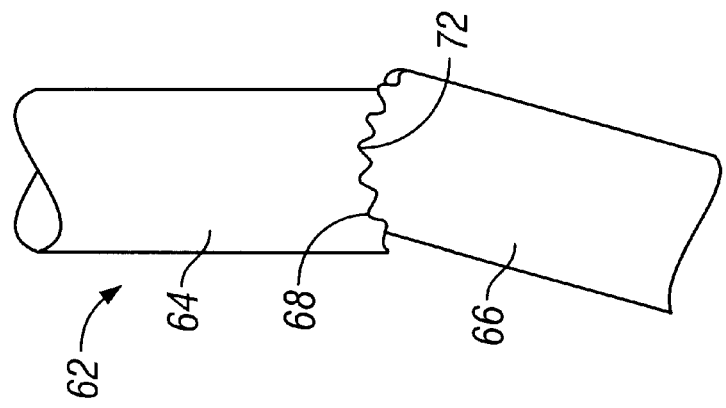
FIGS. 17–18 are views in perspective and partial section of the severed bone sections of FIG. 16 pivoted to correct a deformity according to the present invention.
Figure 17:
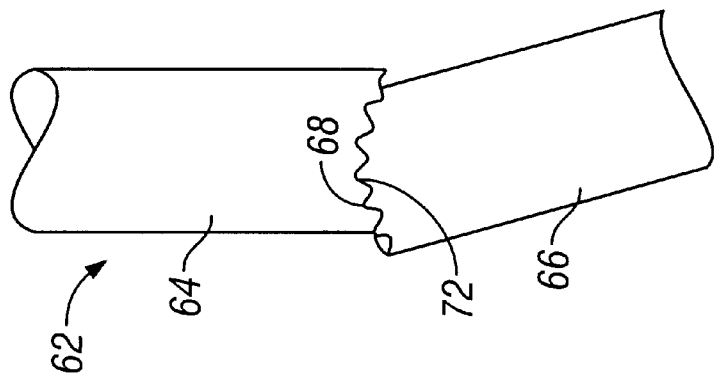
Figure 16:
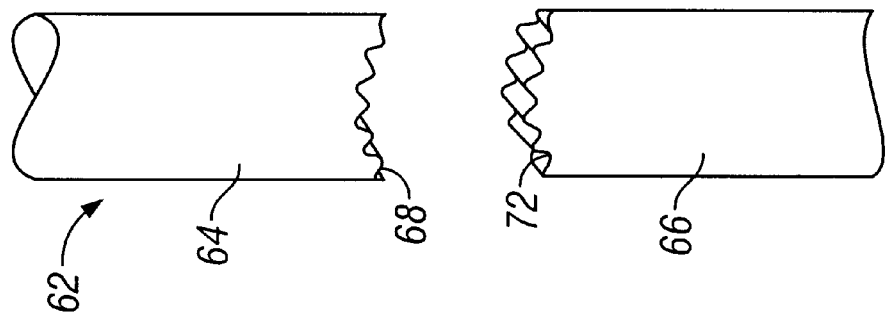
FIG. 16 is a view in perspective and partial section of the bone of FIG. 15 severed by the saw of FIG. 14.

An alternative corrugated blade configuration for power saw 42 is illustrated in FIG. 14. Specifically, blade 6h is similar to blade 6f described above, except that blade 6h has an arcuate or curved configuration and an adapter configured for attachment to another type of conventional power saw. Specifically, power saw 42 is similar to the reciprocating saw described above and includes body 44, handle 46, trigger 48 and blade member 76. The saw, by way of example only, is implemented by a Stryker saw, model 2106. Blade member 76 is substantially similar to blade member 50 described above, but includes an engagement mechanism requiring a different blade adapter configuration as described below. Blade 6h has a generally rectangular blade portion 56 that is curved to form an inverted 'U' shape (e.g., as viewed in FIG. 14). Blade 6h is preferably constructed of stainless steel, but may be constructed of any suitable materials as described above. Blade 6h may be disposable after a single use or autoclaved (e.g., sterilized) for re-use in additional medical procedures, and may be available in a sterile or non-sterile condition. A distal or cutting edge 26 of blade 6h extends along the curved blade dimension and is generally in the form of a sinusoidal wave. Blade 6h includes a plurality of successive blade sections 28, each substantially rectangular and extending between the blade portion proximal and distal edges. The blade sections are arranged to alternately define peaks 30 and valleys 32 between adjacent blade sections, thereby forming the corrugated blade configuration. The corrugated blade configuration typically includes rounded peaks and valleys, however, the peaks and valleys may be formed with any type of rounded, squared or angled configuration. Successive blade sections 28 are typically interconnected at an angle of approximately 90° to form peaks 30, while valleys 32 are formed by adjacent blade sections interconnecting at angles generally greater than 90°. However, the blade sections may be interconnected at any desired angle in the approximate range of 1°–179°, whereby the interconnection angles may be similar or different throughout the blade configuration. Further, the arcuate corrugated blade configuration may include any corrugation frequency or combinations of corrugation frequencies, and any quantity of peaks and valleys. By way of example only, blade 6h includes four peaks and three valleys and has a blade portion transverse dimension between curved portion ends of approximately sixteen millimeters and a length of approximately seven centimeters, however, the blade may be of any size or shape to accommodate various body portions.

Curved or arcuate blade 6h includes an adapter 78 to engage blade member 76 of saw 42. Specifically, adapter 78 is attached to the proximal end of blade portion 56 and is in the form of a generally rectangular elongated bar 80. Transverse projections 82 are attached to and transversely extend from opposite side edges of bar 82. The projections are disposed toward the bar distal end and facilitate engagement of the arcuate blade by the saw blade member.

The arcuate blade configuration described above may be utilized for modification of bone structure as illustrated in FIGS. 15–19. By way of example only, bone 62 (FIG. 15) is initially severed by saw 42 having blade 6h. The saw severs the bone into bone sections 64, 66 and defines mated arcuate corrugated configurations within respective surfaces 68, 72 of bone sections 64, 66 (FIG. 16) corresponding to the configuration of the blade. The severed bone sections are manipulated such that the corrugated pattern of bone section 66 is shifted or rotated to the left (e.g., as viewed in FIG. 17) relative to the pattern of bone section 64 by any desired offset, thereby positioning the bone in a particular orientation to correct a deformity. Either or both bone sections 64, 66 may be manipulated relative to each other to achieve this result.

Conversely, the corrugated pattern of bone section 66 may be shifted or rotated to the right (e.g., as viewed in FIG. 18) relative to the pattern of bone section 64 by any desired offset to position the bone in a particular orientation to correct the deformity. Either or both bone sections 64, 66 may be manipulated relative to each other to achieve this result. Alternatively, bone section 66 may be moved medially or transversely relative to bone section 64 to position the bone to correct a deformity (e.g., as indicated by the double arrow in FIG. 19). In any case, the sawtooth or peak-valley cuts that extend across mating surfaces of bone sections 64, 66 permit those sections to be stably positioned during the knitting or healing process at the bone section interface. The sawtooth cuts also increase the surface area of the mated bone section surfaces, as compared to planar mated surfaces, so that a stronger bond is obtained and the healing time is reduced as described above.

Figure 20:
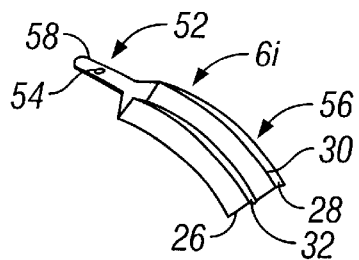
FIG. 20 is a view in perspective of a corrugated blade having a longitudinally curved blade portion for use with a power saw according to the present invention.
Figure 21A:
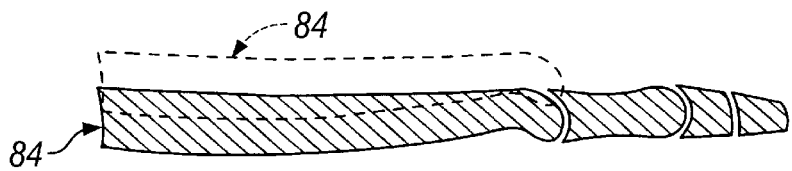
FIG. 21A is a view in elevation and partial section of a bone having a deformity.
Figure 21B:
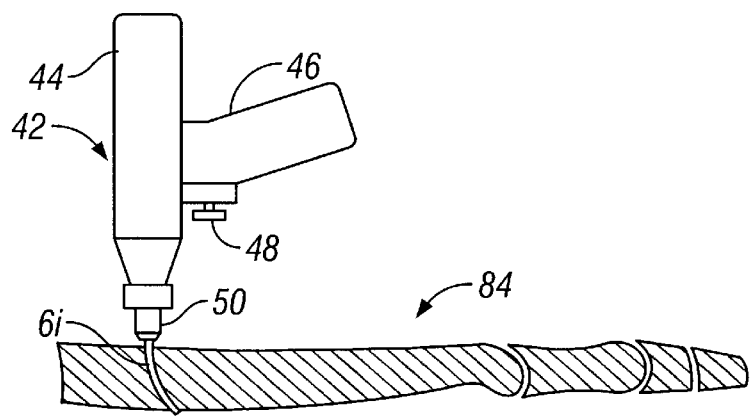
FIG. 21B is a view in elevation and partial section of a saw having the corrugated blade of FIG. 20 severing the bone of FIG. 21A.
Figure 21C:
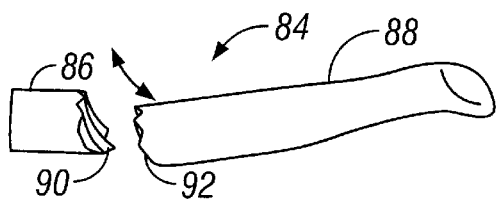
FIG. 21C is a view in perspective of the bone of FIG. 21 A severed by the saw of FIG. 21B.
Figure 21D:
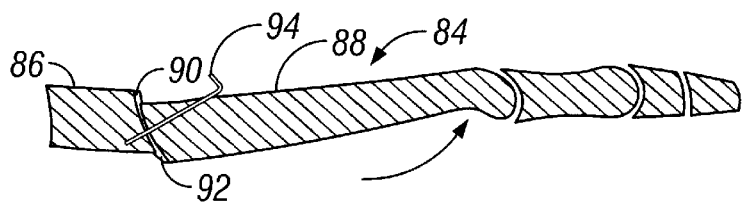
FIG. 21D is a view in elevation and partial section of the severed bone of FIG. 21C manipulated to correct the deformity according to the present invention.

Yet another corrugated blade configuration is illustrated in FIG. 20. Blade 6i is substantially similar to blade 6f described above (FIG. 3B) except that blade 6i has a blade portion that is curved along its longitudinal axis. Specifically, blade 6i has a generally rectangular corrugated blade portion 56 and an adapter 52 attached to the blade portion proximal end. Distal or cutting edge 26 of blade 6i extends along the shorter blade dimension and is generally in the form of a sawtooth wave. Blade portion 56 extends from adapter 52 and curves along its longitudinal axis (e.g., downward relative to adapter 52 as viewed in FIG. 20). Blade 6i includes a plurality of successive blade sections 28, each substantially rectangular having a longitudinal curve as described above and extending between the blade distal edge and adapter 52. The blade sections are arranged to alternatively define peaks 30 and valley 32 between adjacent blade sections as described above. Adapter 52 extends from the blade portion proximal end and tapers to form elongated substantially rectangular bar 58 at its distal portion. Opening 54 is defined in bar 58 toward the bar proximal end to facilitate engagement of blade 6i by saw 42, preferably of the Hall/Zimmer type (FIG. 3A) described above. By way of example only, blade 6i has a length of approximately seven centimeters (e.g., blade portion length of approximately five centimeters and adapter length of approximately two centimeters) and transverse blade portion dimensions of approximately sixteen millimeters, however, the blade may be of any size or shape, while the curve may be at any desired angle to facilitate a particular cut for correcting bone deformities.

An exemplary procedure utilizing blade 6i to modify bone structure is illustrated in FIGS. 21A–21D. Initially, a bone 84 (FIG. 21A) includes a deformity wherein the bone is insufficiently elevated (e.g., the correct bone position being illustrated in phantom). By way of example only, bone 84 (FIG. 21B) is initially severed by saw 42 having blade 6i. The saw severs the bone into bone sections 86, 88 (FIG. 21C) and defines mated arcuate corrugated configurations within respective surfaces 90, 92 of those bone sections corresponding to the configuration of the blade. The severed bone sections are manipulated such that bone section 88 is shifted or slid in a downward direction (e.g., as viewed in FIG. 21D) relative to bone section 86 by a desired offset to raise bone section 88 to the correct position. Once elevated, fixation device 94 may be inserted through bone sections 86, 88 to maintain the bone in the corrected position. The fixation device may be a Kirschner wire, one or more pins or screws or any other fixation devices.

It is to be understood that the bone sections may further be moved or slid transversely (i.e., into or out from the plane of the drawing) relative to each other. Further, the blade may be rotated one hundred eighty degrees and utilized in order to produce a cut in an opposite direction. In any case, the sawtooth or peak-valley cuts that extend across surfaces 90, 92 of bone sections 86, 88 permit those sections to be stably positioned during the knitting or healing process at the bone section interface. The sawtooth cuts also increase the surface area of the mated bone section surfaces, as compared to planar mated surfaces, so that a stronger bond is obtained and the healing time is reduced.

Figure 22:
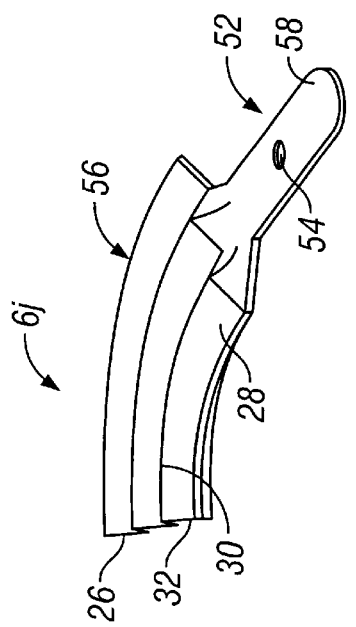
FIG. 22 is a view in perspective of a corrugated blade having a transversely curved blade portion for use with a power saw according to the present invention.

A further corrugated blade configuration is illustrated in FIG. 22. Blade 6j is substantially similar to blade 6i described above (FIG. 20), except that blade 6j has a blade portion having a transverse curve. Specifically, blade 6j has generally rectangular corrugated blade portion 56 and an adapter 52 attached to the blade portion proximal end. Distal or cutting edge 26 of blade 6j extends along the shorter blade dimension and is generally in the form of a sawtooth wave. Blade portion 56 extends distally from adapter 52 and curves transversely (e.g., toward the left as viewed in FIG. 22). Blade 6j includes a plurality of successive blade sections 28, each substantially rectangular having a transverse curve as described above and extending between the blade distal edge and adapter 52. The blade sections are arranged to alternately define peaks 30 and valleys 32 between adjacent blade sections as described above. Adapter 52 extends from the blade portion proximal end and tapers to form elongated generally rectangular bar 58 at its distal end. Opening 54 is defined in bar 58 toward the bar distal end to facilitate engagement of blade 6j by saw 42, preferably of the Hall/Zimmer type (FIG. 3A) described above. The blade may be of any size or shape, while the curve may be at any desired angle to facilitate a particular cut for correcting bone deformities.

Figure 23A:
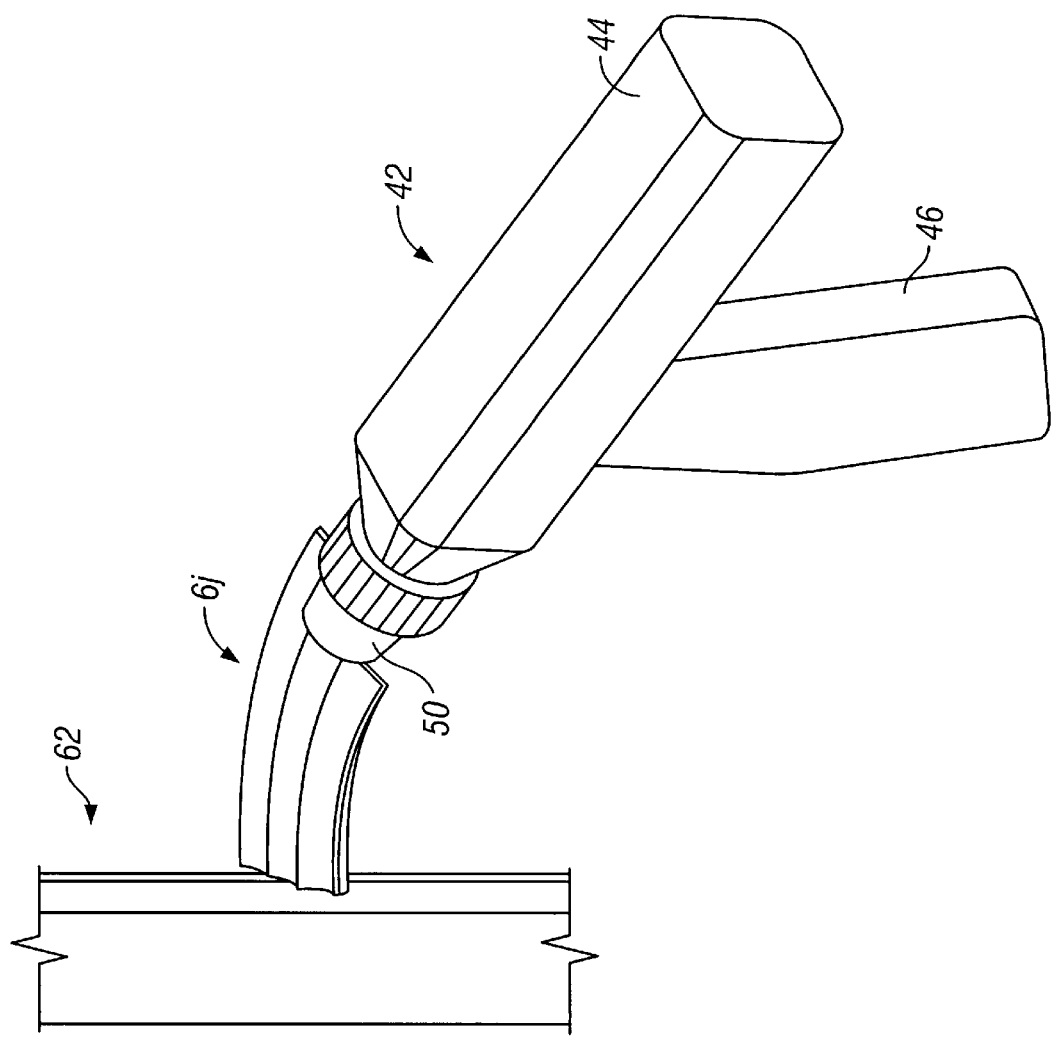
FIG. 23A is a view in perspective of a saw having the corrugated blade of FIG. 22 severing a bone.
Figure 23B:
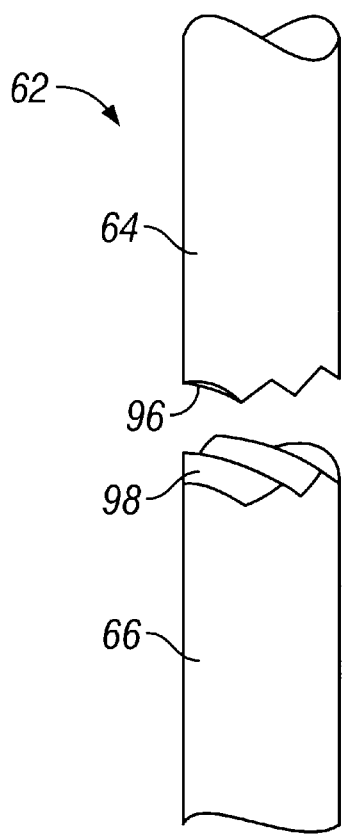
FIG. 23B is a view in perspective and partial section of the bone of FIG. 23A severed by the corrugated blade of FIG. 22.
Figure 23C:
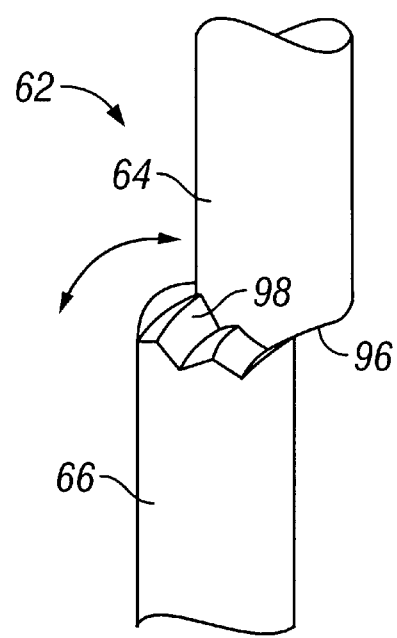
FIG. 23C is a view in perspective and partial section of the severed bone sections of FIG. 23B manipulated to correct a deformity according to the present invention.

Corrugated blade 6j be utilized for modification of bone structure as illustrated in FIGS. 23A–23C. By way of example only, bone 62 (FIG. 23A) is initially severed by saw 42 having blade 6j. The saw severs the bone into bone sections 64, 66 (FIG. 23B) and defines mated curved corrugated configurations within respective surfaces 96, 98 of those bone sections corresponding to the configuration of the blade. The severed bone sections are manipulated such that the bone section 96 is shifted or slid rearward (e.g., as viewed in FIG. 23C) relative to bone section 66 by a desired offset. The curved corrugated patterns within the bone section surfaces rotate bone section 64 during the shift to position the bone in a desired orientation to correct a deformity. Bone section 64 may be shifted frontward (e.g., as indicated by the double arrow in FIG. 23C) to rotate the bone section in the opposite direction. Either or both bone sections 64, 66 may be manipulated relative to each other to achieve the desired orientation.

It is to be understood that the bone sections may be moved transversely (i.e., left or right as viewed in FIG. 23C) relative to each other. Further, the blade may be rotated one-hundred eighty degrees and utilized in order to produce a cut in an opposite direction. In any case, the sawtooth or peak-valley cuts that extend across surfaces 96, 98 of bone sections 64, 66 permit those sections to be stably positioned during the knitting or healing process at the bone section interface. The sawtooth cuts also increase the surface area of the mated bone section surfaces, as compared to planar mated surfaces, so that a stronger bond is obtained and the healing time is reduced.

Figure 24B:
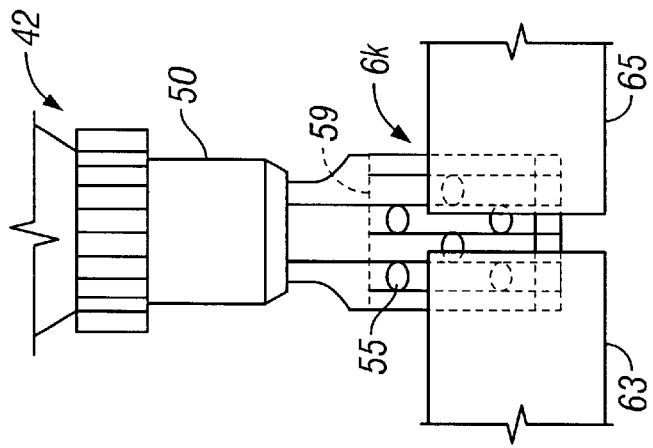
FIG. 24B is a view in perspective and partial section of the staple inserted within a bone according to the present invention.
Figure 24A:
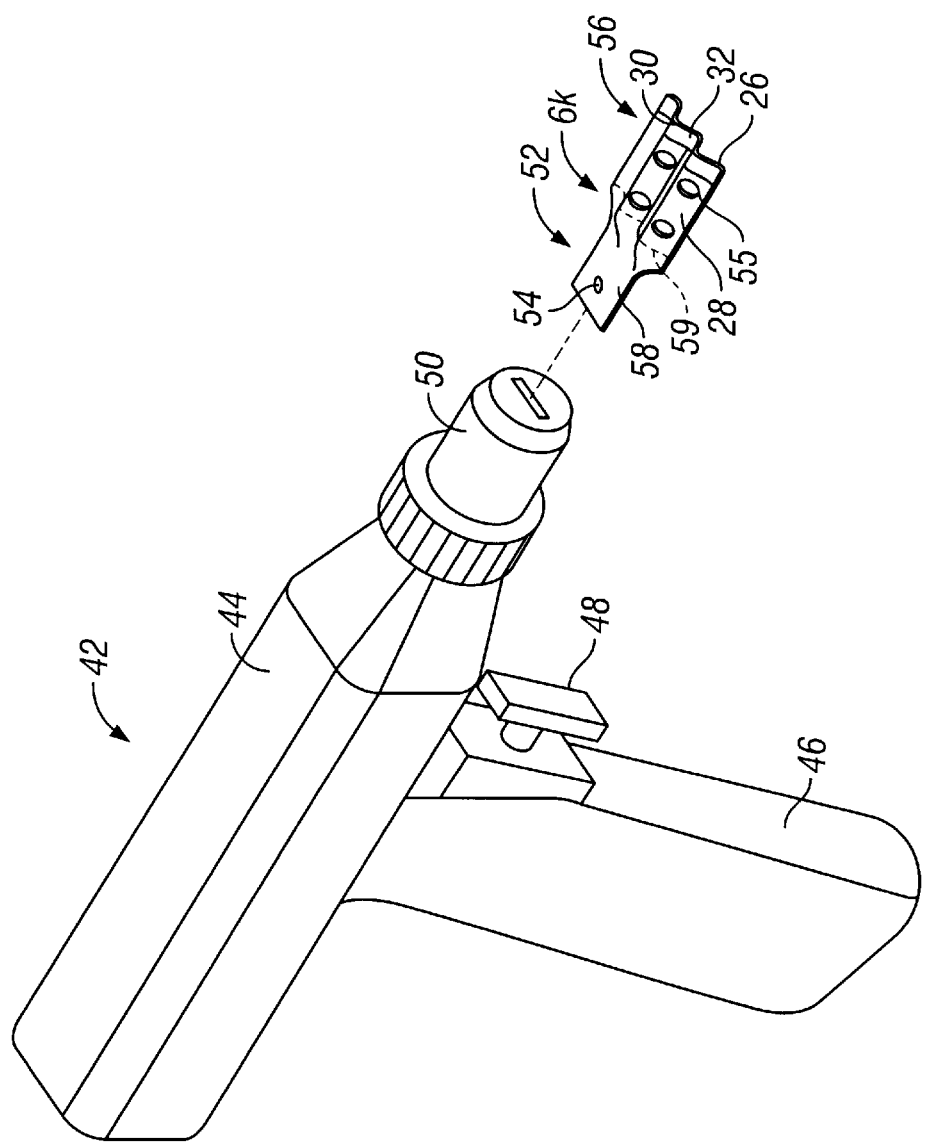
FIG. 24A is an exploded view in perspective of a corrugated blade configured for use as a staple and employed by a power saw according to the present invention.

The corrugated blade may be configured in the form of a staple as illustrated in FIG. 24A. Blade 6k is substantially similar to blade 6g described above (FIG. 3C) except that the blade portion is detachable and includes a series of openings defined therein. Specifically, blade 6k has generally rectangular corrugated blade portion 56 and an adapter 52 attached to the blade portion proximal end. Distal or cutting edge 26 of blade 6k extends along the shorter blade dimension and is generally in the form of a sawtooth wave. Blade portion 56 includes a transverse perforation or partial cut 59, preferably formed by a laser, defined therein toward adapter 52 to detach the blade portion from the adapter during use as described below. Blade 6k includes a plurality of successive blade sections 28, each substantially rectangular and extending between the blade distal edge and adapter 52. The blade sections are arranged to alternately define peaks 30 and valleys 32 between adjacent blade sections as described above. Holes 55 are defined within the blade sections to enable the bone to grow through the holes during healing. The holes may be randomly spaced or arranged in any desired fashion. Adapter 52 extends from the blade portion proximal end and tapers to form elongated substantially rectangular bar 58 at its distal portion. Opening 54 is defined in bar 58 toward the bar proximal end to facilitate engagement of staple 6k by saw 42, preferably of the Hall/Zimmer type (FIG. 3A) described above. The staple may be of any size or shape and have an adapter configured for any manual or power tool usage as described above.

The staple may be utilized for attachment of bone sections as illustrated in FIG. 24B. By way of example only, staple 6k is initially inserted into bone sections 63, 65 by saw 42 in order to attach the bone sections together. Once the staple is inserted, the saw is manipulated about perforation 59 to detach adapter 52 from blade portion 56, thereby leaving the blade portion within the bone sections. The bone sections heal and grow through openings 55 to securely attach the bone sections to each other. The staples may be utilized as an alternative to utilizing a rod or pole to reinforce the spine. Any of the blades described above may be utilized to remove the staple by severing the bone sections on each side of the staple, removing the section of bone containing the staple, and placing the severed sections together in a mated fashion due to the corrugated patterns as described above.

Figure 25:
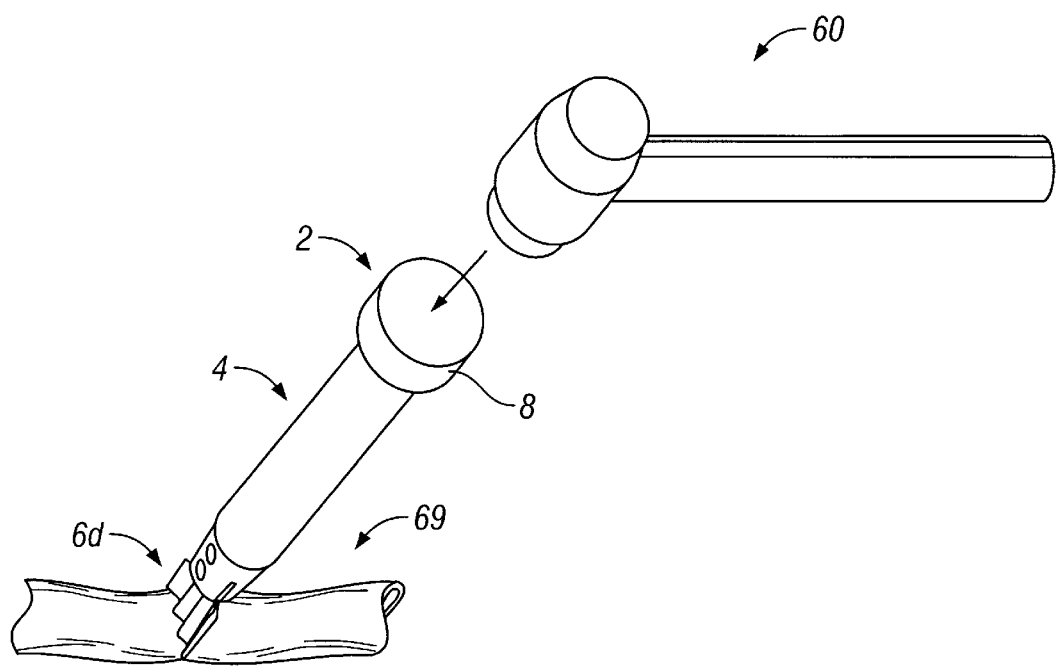
FIG. 25 is an exploded view in perspective of an osteotome having a corrugated blade severing a vein according to the present invention.
Figure 26A:
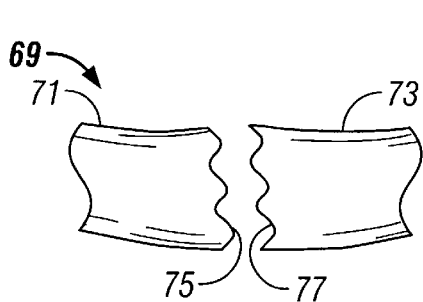
FIG. 26A is a view in perspective and partial section of the vein of FIG. 25 severed by the osteotome.
Figure 26B:
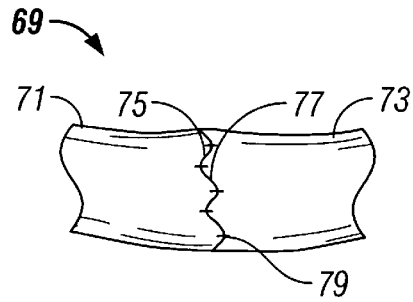
FIG. 26B is a view in perspective of the severed vein sections of FIG. 26A coupled in a mated fashion according to the present invention.

The corrugated blade configurations described above may further be utilized on other anatomical structures (e.g., veins, arteries, bowels, soft tissue, etc.) as illustrated in FIGS. 25 and 26A–26B. By way of example only, a vein 69 (FIG. 25) is initially severed by osteotome 2 having blade 6d (e.g., in an anastamosis procedure). The osteotome severs the vein into vein sections 71, 73 (FIG. 26A) and defines mated corrugated configurations within respective surfaces 75, 77 of the vein section peripheries. The severed vein sections are reunited such that the corrugated pattern of vein section 71 is interleaved with the pattern of vein section 73. Sutures 79 are applied to the vein sections to maintain those sections in an attached state. The sawtooth or peak-valley cuts that extend across the mating surfaces of vein sections 71, 73 permit those sections to be reunited with enhanced closure, thereby reducing the chance for leaking at the contact site. The sawtooth cuts also increase the surface area of the mated vein section surfaces so that a stronger bond is obtained and the healing time is reduced.

Still another corrugated blade configuration is illustrated in FIG. 27. Specifically, blade 6m is substantially similar to blade 6g (FIG. 3C) described above, except that blade 6m has a helical or torsional configuration and a greater transverse blade portion dimension. Blade 6m includes blade portion 56 that is generally rectangular and twisted at an approximate 45° angle relative to a longer dimension blade axis, thereby providing a helical or torsional blade configuration. Distal or cutting edge 26 of blade 6m extends along the shorter blade dimension and is generally in the form of a sinusoidal wave. Blade 6m includes a plurality of successive blade sections 28, each generally rectangular, twisted at a slight angle and extending between the blade portion proximal and distal edges. The blade sections are arranged to alternately define peaks 30 and valleys 32 between adjacent blade sections as described above. Adapter 52 extends from the blade portion proximal end and tapers to form an elongated substantially rectangular bar 58 at its distal portion. Opening 54 is defined in bar 58 toward the bar proximal end to facilitate engagement of blade 6m by saw 42, preferably of the Hall/Zimmer type (FIG. 3A) described above. Blade 6m typically permits manipulation of bone sections as described above to correct deformities (e.g., length, orientation, lateral position, etc.). The corrugated blade configuration may be twisted at any desired angle and may be of any shape or size. Further, the blade may be adapted for manual use or for use with power tools as described above.

Certain medical procedures performed on bone or other anatomical structures may be more suited for a blade having a planar blade or cutting portion. For example, a planar blade may be utilized for amputations or for removing a section of bone or an irregular bone growth. An exemplary planar blade is illustrated in FIG. 28. Initially, conventional planar blades are typically operated manually and have dimensions that prevent the blades from cutting entirely through bones (e.g., bones having transverse dimensions greater than approximately one inch). Accordingly, the planar blades of the present invention are configured for use with power saws and to cut entirely through these bones for various procedures, such as amputations. Blade 7a is similar to blade 6f (FIG. 3B) described above except that blade 7a has a planar blade portion. Specifically, blade 7a has a generally rectangular blade portion 82 and an adapter 81 attached to the blade portion proximal end. The adapter is substantially similar to adapter 52 described above. A distal or cutting edge 27 of blade 7a extends along the shorter blade dimension and is tilted at a slight rearward angle. The blade portion is elongated to facilitate cutting entirely through bone and has a length of approximately three centimeters. Adapter 81 extends from the blade portion proximal end and tapers to form an elongated substantially rectangular bar 85 at its distal portion. An opening 87 is defined in bar 85 toward the bar proximal end to facilitate engagement of blade 7a by saw 42, preferably of the Hall/Zimmer type (FIG. 3A) described above. The blade may be of any shape or size, and may be adapted for manual use or for use with power tools as described above.

Alternative planar blade configurations are illustrated in FIGS. 29–31. These blades are substantially similar to blade 7a described above, but have configurations to maintain blade position on the bone during severance. For example, blade 7b (FIG. 2A) has a projection 89 attached to and extending distally from the approximate center of cutting edge 27. Projection 89 is in the form of an arrowhead or point to engage the bone. Blade 7c (FIG. 30) has cutting edge 27 defined along an arcuate recess formed in the blade portion distal end. The cutting edge or recess surrounds the bone to maintain the blade position on the bone during severance. Blade 7d (FIG. 31) includes a blade portion 83 having a curve in a longitudinal direction to similarly maintain the blade position on the bone. These blades may be of any shape or size and may be configured for manual use or for use with power tools as described above.

Figure 32:
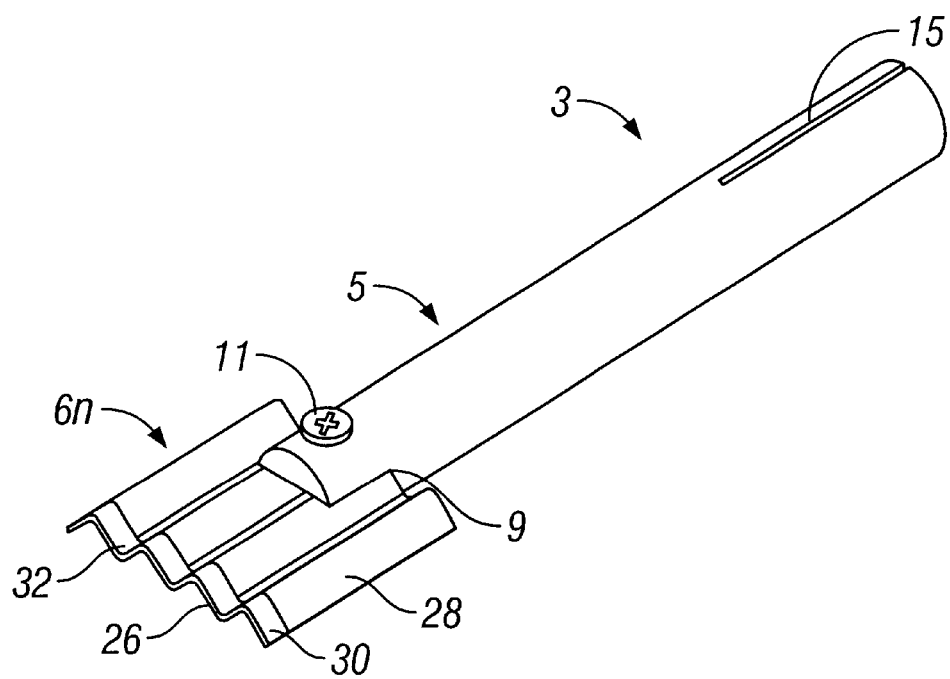
FIG. 32 is a view in perspective of an alternative osteotome having a corrugated blade according to the present invention.

An alternative corrugated blade for manual use with an osteotome according to the present invention is illustrated in FIG. 32. Specifically, an osteotome 3 includes a handle 5 and a blade 6n disposed at the handle distal end. Handle 5 is substantially cylindrical and includes a transverse blade receiving slot 9 defined therein toward a central portion of the handle distal end surface. The handle typically has a length of approximately ten centimeters, but may be of any shape or size. The blade slot extends proximally from the handle distal end surface for a slight distance and receives blade 6n to secure the blade to the handle. The blade is generally inserted within blade receiving slot 9, whereby a screw 11 or other fastener is inserted transversely through a handle opening (not shown) to secure the blade to the handle as described below. A longitudinal tool slot 15 is defined in the handle toward a central portion of the handle proximal edge and orthogonal to blade slot 9. The tool slot extends distally from the handle proximal edge for a slight distance and enables handle 5 to interconnect to a power tool for severing a bone.

Blade 6n is substantially similar to corrugated blades 6a–6d described above except that blade 6n is secured to the handle by screw 11 without the use of openings defined in the blade. Specifically, blade 6n has a generally rectangular periphery with a distal or cutting edge 26 extending along the longer blade dimension and generally in the form of a sawtooth wave. The blade includes a plurality of successive blade sections 28, each substantially rectangular and extending between the blade proximal and distal edges. The blade sections are arranged to alternately define peaks 30 and valleys 32 between adjacent blade sections, thereby forming the corrugated blade configuration. By way of example only, blade 6n includes four peaks and three valleys and has a longer blade dimension of approximately 3.3 centimeters and a shorter blade dimension between the blade proximal and distal edges of approximately 3.0 centimeters; however, the blade may be of any size or shape to accommodate various body portions.

Figure 33:
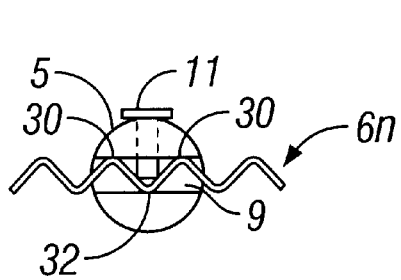
FIG. 33 is a front view in elevation of the osteotome of FIG. 32 illustrating the manner in which the corrugated blade is secured to an osteotome handle.

Blade 6n is typically secured to handle 5 via screw 11 as illustrated in FIG. 33. Specifically, the proximal end of blade 6n is inserted within blade slot 9 with the blade distal or cutting edge extending distally of the handle. The blade slot typically has dimensions sufficient to receive and contain a valley 32 and two adjacent peaks 30, whereby the blade is positioned within the slot such that screw 11 is aligned with a valley 32 preferably located at the central portion of the blade. Screw 11 is inserted through the handle opening and penetrates the blade slot and central valley to contact and apply force to the blade in the aligned valley 32, thereby securing the blade within the slot between the screw and a slot side wall. The valley and peaks disposed within the blade slot contact the slot side walls to provide three points of contact between the blade and handle, thereby securing the blade to the handle and preventing blade movement relative to the handle during use. Alternatively, the screw may be aligned with other blade valleys to provide the osteotome with an asymmetrical blade configuration for use in specific applications. The handle may include any quantity of screws or other fastening devices to secure the blade to the handle.

Figure 34:
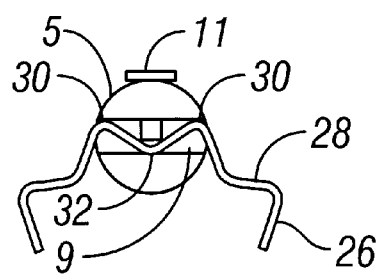
FIG. 34 is a front view in elevation of the osteotome of FIG. 32 illustrating the manner in which an arcuate corrugated blade is secured to the handle.

An alternative corrugated blade configuration for osteotome 2 is illustrated in FIG. 34. Specifically, blade 6p is substantially similar to blade 6n described above, except that blade 6p has an arcuate or curved configuration. Blade 6p has a generally rectangular periphery but is curved to form an inverted 'U' shape (e.g., as viewed in FIG. 34). A distal or cutting edge 26 of blade 6p extends along the curved blade dimension and is generally in the form of a sinusoidal wave. Blade 6p includes a plurality of successive blade sections 28, each substantially rectangular and extending between the blade proximal and distal edges. The blade sections are arranged to alternately define peaks 30 and valleys 32 between adjacent blade sections, thereby forming the corrugated blade configuration. By way of example only, blade 6p includes four peaks and three valleys and has a blade dimension between curved portion ends of approximately 2.8 centimeters and a longer blade dimension between the blade proximal and distal edges of approximately 3.0 centimeters, however, the blade may be of any size or shape to accommodate various body portions.

Blade 6p is secured to handle 5 via screw 11 in substantially the same manner described above for blade 6n. The proximal end of blade 6p is inserted within blade slot 9 with the blade distal or cutting edge extending distally of the handle. The blade slot typically has dimensions sufficient to contain a valley 32 and two adjacent peaks 30, whereby the blade is positioned within the slot such that screw 11 is aligned with a valley 32 preferably located at the central portion of the blade. Screw 11 is inserted through the handle opening and penetrates the blade slot at the central valley 32 to contact and apply force to the blade, thereby securing the blade within the slot between the screw and a slot side wall. The valley and peaks disposed within the blade slot contact the slot side walls to provide three points of contact between the blade and handle, thereby securing the blade to the handle and preventing blade movement relative to the handle during use. Alternatively, the screw may be aligned with other blade valleys to provide the osteotome with an asymmetrical blade configuration for use in specific applications. The handle may include any quantity of screws or other fastening devices to secure blade 6n to the handle.

The above-described corrugated blades are not limited to the specific applications disclosed herein, but may be utilized for various general surgical procedures. For example, the blades may be utilized for performing amputations and/or removing diseased bone in the manner described above. Basically, the blades are utilized to place cuts in the bone at locations that encompass or surround the diseased section. The diseased portion is removed, while the severed bone sections are reunited in mated fashion as described above. Further, the corrugated blades may be utilized to perform arthrodesis procedures to stiffen joints in humans or animals (e.g., to attach two joint components together). In particular, the corrugated blades may be utilized to sever bones of a joint and then reunite the bones in a mated fashion as described above. The resulting healed bone is stronger and provides a stiffer joint. Moreover, the corrugated blades may be utilized for fracture repair in humans and animals where cuts are made at locations that encompass or surround the fractured section. The fractured portion is removed, while severed bone sections are reunited in mated fashion as described above. Alternatively, the staple may be utilized as described above for fixation of fractures (e.g., hold fractured bone together) and arthrodesis (e.g., stiffen joints) for bones in humans and animals.

In addition, the corrugated blades may be utilized with other anatomical structures. For example, the corrugated blades may be used as described above for soft tissue repair in tendons, ligaments, joint capsules and muscles, with arteries and veins (e.g., surgical anastomosis procedures), bowels or other structures of humans and animals. The corrugated blades basically sever those items for enhanced stability and healing when the severed sections are reunited.

It is to be understood that bones or other anatomical structures may be severed in various fashions and with more than one blade. For example, two corrugated blades may be utilized each having a different corrugation frequency and/or angle of severance to divide a bone into respective bone sections. The plurality of bone surface corrugations defined by the blades provide increased surface area for healing and enhanced bone stability. Further, the osteotomes described above may include a pair of corrugated blades (e.g., a pair of blades 6a) arranged in a 'V'-shaped configuration. The pair of blades sever the bone and essentially form a portion of the bone into a wedge shape that may be removed to reduce the bone length. The corrugated blades form mated step configurations within severed bone section surfaces as described above to enable the severed bone sections to be coupled in a mated fashion after removal of the wedge portion. This type of arrangement may be similarly adapted for use with power tools as described above.

In addition, the corrugated blades may include various configurations to accommodate various body portions. The osteotomes and/or various corrugated and planar blades described above may be assembled into a kit for use in connection with various medical procedures. The kits may include multiple blades specifically directed to a particular bone size or anatomical structure, or may include a complete set of blades for use with plural bone sizes and/or other structures. Further, the kits may include any portion of the above-described kits to accommodate any combination of bones (e.g., lower extremities, upper extremities, spinal areas, etc.) and/or structures. The kits may further include tools associated with the blades, such as various handles, mallets and/or power tools, to utilize the blades in various applications.

It is to be understood that the terms "up", "down", "right", "left", "top", "bottom", "front", "rear","side", "upper", "lower", "length", "width", "height" and the like are used herein merely to describe points of reference and do not limit the present invention to any particular configuration or orientation.

It will be appreciated that the embodiments described above and illustrated in the drawings represent only a few of the many ways of implementing a corrugated osteotome blade and method of severing bones and other anatomical structures.

The corrugated and planar blades may be of any shape or size, and are preferably constructed of stainless steel. However, the corrugated and planar blades may be manufactured from flat rolled material, wire, round material, bar type or any other suitable materials (e.g., titanium). The osteotome, handle and corrugated and planar blades may, either individually or in any combination, be disposable after a single use or be sterilized for re-use in subsequent procedures, and may be available in a sterile and non-sterile condition. The corrugated blades may each include any corrugation frequency, any combination of corrugation frequencies, or any quantity of peaks and valleys to form symmetrical or asymmetrical blade configurations. The blade sections of the corrugated blades may interconnect at any desired angles to form the corrugated configurations (e.g., peaks and valleys). The peaks and valleys may be rounded, formed in a square-like configuration, or angled in any desired fashion (e.g., to form 'V' and inverted 'V' configurations, etc.).

The corrugated blades may be curved, twisted or otherwise configured in any fashion at any desired angles, and may include any shaped configuration and/or any combination of these features. The corrugated and planar blades may include any quantity of openings of any shape or size and disposed at any suitable locations to enable attachment of the blades to an osteotome handle or power tool. The osteotomes described above may include any quantity of corrugated and planar blades oriented at any desired angles, whereby the blades may each include any configuration (e.g., corrugated, planar, non-planar, etc.) or combination of configurations. Similarly, a blade may include several individual corrugated and/or planar blades having any of the blade configurations described above and be configured for use with a power tool. The corrugated and planar blades may be configured for use with an osteotome or a power tool and include any conventional or other attachment mechanism or adapter (e.g., clamps, locking mechanism, hooks, the mechanisms described above, etc.). The corrugated and planar blades may include any combination of or individual blade configurations described above, and may be utilized for any type of surgical procedures.

The corrugated blade in the form of a staple may include any quantity of perforations disposed at any suitable locations. The perforations may be defined in the staple by any suitable techniques (e.g., formation of the staple, laser, cutting blades, etc.). The staple may include any quantity of holes of any shape or size disposed at any suitable locations. The staple may include any conventional or other detachment mechanisms (e.g., fasteners, clasps, hooks, etc.) to facilitate placement of the staple in bone or other anatomical structure.

The planar blades may include any suitable configuration enhancing engagement with a bone. The planar blades may include any quantity of points or recesses of any shape or size and disposed at any suitable locations, and may be curved at any desired angle.

The osteotome handle, head and blade attachment member may be of any shape or size, and may be constructed of any suitable materials. The handle may engage the corrugated or planar blades via any conventional or other securing techniques (e.g., screws, clamps, locking mechanism, brackets, etc.). Alternatively, the corrugated and planar blades may be formed integral with the handle. The handle may include any quantity of openings of any shape or size disposed at any suitable locations. The attachment member sections may include any configuration suitable to engage a blade. The nuts and bolts may be of any quantity, shape or size, and may be implemented by any types of fastening devices. The handle may accommodate any quantity of corrugated and/or planar blades having any of the blade configurations described above.

The alternative osteotome handle may be of any shape or size, and may be constructed of any suitable materials. The alternative osteotome handle may engage the corrugated or planar blades via any conventional or other securing techniques (e.g., screws, clamps, locking mechanism, brackets, etc.). Alternatively, the corrugated and planar blades may be formed integral with that handle. The alternative osteotome handle may accommodate any quantity of corrugated and/or planar blades having any of the blade configurations described above. The fastening screw function may be implemented by any conventional screw or any other fastening device, whereby any quantity of screws may be utilized to secure a blade to the alternative osteotome handle. The screw may contact any blade portion to secure a blade to that handle. The alternative osteotome handle may include any quantity of blade and tool slots, whereby these slots may be of any shape or size, and may be defined in the handle at any location. The osteotome handles described above may be utilized with any type of hammer, mallet or other instrument suitable for driving the blades through the bone or other anatomical structure, while the alternative osteotome handle may further engage a power tool.

The corrugated and planar blades may be oriented at any desired angle for severing bone or other anatomical structures. The severed bone sections may be manipulated in any fashion (e.g., displaced by any offset) to lengthen or shorten the bone, to position the bone in a particular orientation, to elevate or lower the bone or to correct any other type of deformity. The bone or anatomical structures may be severed utilizing any quantity of corrugated and/or planar blades or cuts, whereby the blades may include varying corrugation frequencies or other configurations to securely couple the severed bone sections for healing.

The corrugated and planar blades may be configured for use with and have an adapter for any type of power tool or saw. The adapter may have any configuration suitable to interface any power tool, and may be constructed of any suitable materials. The adapter bar may be of any size or shape and may be disposed at any suitable locations, while the adapter projections may be of any quantity, size or shape and may be disposed at any suitable locations. The adapter and blades may be formed integral or as separate components permanently or removably attached to each other. In the latter case, the corrugated and planar blades may be interchangeable with a single adapter accommodating the blades. The power tool may accommodate any quantity of corrugated and/or planar blades. The corrugated and/or planar blades may be rotated at any desired angle and placed in the tool to produce a cut at any particular angle or orientation.

The corrugated and planar blades may be configured to accommodate various body portions or anatomical structures of humans and/or animals, and may further be utilized for other materials, such as wood or plastics. The corrugated and planar blades may be modified in any fashion (e.g., curved, twisted, etc.) and may have any portion thereof configured in a corrugated manner (e.g., a blade may be fully or partially corrugated). The corrugated and/or planar blades may be assembled into various kits, whereby the kits may include any quantity of osteotomes, corrugated and/or planar blades or associated tools (e.g., hammer, power tool, etc.), or any combination of these items. The kits may be specifically designed for specific body portions or may include components for accommodating the entire body. The kits or any portion thereof may be disposable after a single use or be sterilized for re-use in subsequent medical procedures, and may be available in a sterile or non-sterile condition.

The corrugated and planar blades may be utilized for any types of surgical procedures requiring severing, cutting or removing of sections of anatomical structures. The corrugated and/or planar blades are not limited to the specific procedures described herein, but may be utilized in any manner to sever, cut and/or remove sections of anatomical or other structures.

From the foregoing description, it will be appreciated that the invention makes available a novel corrugated osteotome blade and method of severing bones and other anatomical structures wherein a blade having a corrugated configuration severs bone and other anatomical structures and provides a mated pattern within the severed sections to enhance stability and promote healing when the sections are reunited.

Having described preferred embodiments of a new and improved corrugated osteotome blade and method of severing bones and other anatomical structures, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. In a medical instrument for severing anatomical structures, a blade for cutting said structures comprising:

a cutting member including a body with transverse edges and proximal and distal ends, said cutting member including a corrugated cutting edge defined along a distalmost edge of said body between said transverse edges and of a sharpness to sever said anatomical structures, wherein said blade is interchangeable and said cutting member is removably securable to a distal end of said medical instrument.

2. The blade of claim 1 wherein said anatomical structures include bone.

3. The blade of claim 1 wherein said anatomical structures include blood vessels.

4. The blade of claim 1 wherein said anatomical structures include soft tissue.

5. The blade of claim 1 wherein said cutting member body is corrugated between said transverse edges.

6. The blade of claim 5 wherein said cutting member body is arcuate between said transverse edges.

7. The blade of claim 5 wherein said cutting member body includes a curve extending along its transverse axis.

8. In a medical instrument for severing anatomical structures, a blade for cutting said structures comprising:

a cutting member securable to a distal end of said medical instrument and including a body with transverse edges and proximal and distal ends, said cutting member including a corrugated cutting edge defined along a distalmost edge of said body between said transverse edges;

wherein said cutting member body is corrugated between said transverse edges and includes a curve extending along its longitudinal axis.

9. In a medical instrument for severing anatomical structures, a blade for cutting said structures comprising:

a cutting member securable to a distal end of said medical instrument and including a body with transverse edges and proximal and distal ends, said cutting member including a corrugated cutting edge defined along a distalmost edge of said body between said transverse edges; and a securing mechanism disposed toward said cutting member body proximal end to attach said cutting member to said medical instrument.

10. The blade of claim 9 wherein said cutting member body includes a plurality of openings defined therein and a detachment mechanism to detach said cutting member body from said securing mechanism when said cutting member body is inserted within said structures.

11. The blade of claim 10 wherein said detachment mechanism includes a perforation defined in said cutting member body.

12. The blade of claim 9 wherein said medical instrument includes a handle and said securing mechanism includes at least one opening defined in said cutting member body to attach said cutting member to said handle.

13. The blade of claim 9 wherein said medical instrument includes a power tool and said securing mechanism includes an adapter to attach said cutting member to said power tool.

14. The blade of claim 13 wherein said adapter includes an elongated bar attached to and extending from said cutting member body proximal end, wherein said bar includes an opening defined therein to secure said cutting member to said power tool.

15. The blade of claim 13 wherein said adapter includes an elongated bar attached to and extending from said cutting member body proximal end, wherein said bar includes a plurality of projections extending transversely from said bar to secure said cutting member to said power tool.

16. An osteotome kit comprising:

a plurality of interchangeable blades each removably securable to a medical instrument and of a sharpness to sever anatomical structures, wherein said kit includes at least one blade with a cutting member including a body with transverse edges and proximal and distal ends, said cutting member including a corrugated cutting edge defined along a distalmost edge of said body between said transverse edges.

17. The kit of claim 16 wherein at least one blade includes a planar cutting edge.

18. The kit of claim 16 wherein at least one blade includes a cutting member body that is arcuate between its transverse edges.

19. The kit of claim 16 wherein at least one blade includes a cutting member body that has a curve extending along its longitudinal axis.

20. The kit of claim 16 wherein at least one blade includes a cutting member body that has a curve extending along its transverse axis.

21. The kit of claim 16 further including at least one medical instrument to manipulate at least one of said blades to penetrate an anatomical structure.

22. An osteotome for severing anatomical structures comprising:

a blade comprising a cutting member including a body with transverse edges and proximal and distal ends, said cutting member further including a corrugated cutting edge defined along a distalmost edge of said body between said transverse edges and of a sharpness to sever said anatomical structures; and a handle receiving said blade and including an impact section disposed within a handle proximal portion to receive impact forces applied by an object to said handle to drive said blade into said anatomical structure.

23. The ostetome of claim 22 wherein said handle further includes a blade attachment member for receiving and securing said blade to said handle.

24. An osteotome for severing anatomical structures comprising:

a blade comprising a cutting member including a body with transverse edges and proximal and distal ends, said cutting member further including a corrugated cutting edge defined along a distalmost edge of said body between said transverse edges; and a handle for receiving said blade and facilitating penetration of an anatomical structure, said handle including a blade attachment member for receiving and securing said blade to said handle;

wherein said cutting member body includes at least one opening defined therein and said blade attachment member includes plural engagement sections each having at least one opening defined therein for receiving a fastening device, wherein said engagement sections encompass said blade with said fastening device inserted through said openings of said blade and engagement sections to secure said blade to said handle.

25. An osteotome for severing anatomical structures comprising:
   a blade comprising a cutting member including a body with transverse edges and proximal and distal ends, said cutting member further including a corrugated cutting edge defined along a distalmost edge of said body between said transverse edges; and
   a handle for receiving said blade and facilitating penetration of an anatomical structure, said handle including a blade attachment member for receiving and securing said blade to said handle;
   wherein said blade attachment member includes a slot defined in said handle for receiving said blade and a fastening device inserted through said handle to apply force to said blade to secure said blade in said slot.

26. In a medical instrument for severing bones, a blade for cutting said bones comprising:
   a cutting member securable to a distal end of said medical instrument and including a body with transverse edges and proximal and distal ends, said cutting member including a cutting edge defined along a distalmost edge of said body between said transverse edges and of a sharpness to sever bones, wherein said cutting edge includes a deformity configured to engage a bone and restrict displacement of said cutting edge on said bone during said cutting.

27. The blade of claim 26 wherein said deformity includes a point extending distally from said cutting edge.

28. The blade of claim 26 wherein said deformity includes a recess extending from said cutting edge partially into said cutting member body.

29. The blade of claim 26 wherein said cutting member body includes a curve extending along its longitudinal axis and said deformity includes said cutting edge oriented at an angle in accordance with said curve.

30. A method of structurally enhancing anatomical structures comprising the steps of:
   (a) forming corrugated patterns within adjacent sections of an anatomical structure by cutting said structure via a blade including a cutting member having a body with transverse edges and proximal and distal ends, wherein said cutting member includes a corrugated cutting edge defined along a distalmost edge of said body between said transverse edges; and
   (b) manipulating said severed sections into a desired position and coupling said severed sections in a mated fashion via said corrugated patterns.

31. The method of claim 30 wherein step (a) further includes:
   (a.1) forming corrugated patterns within adjacent sections of said anatomical structure by cutting said structure via said blade, wherein said cutting member body is arcuate between said transverse edges.

32. The method of claim 30 wherein step (a) further includes:
   (a.1) forming corrugated patterns within adjacent sections of said anatomical structure by cutting said structure with said blade, wherein said cutting member body includes a curve extending along its longitudinal axis.

33. The method of claim 30 wherein step (a) further includes:
   (a.1) forming corrugated patterns within adjacent sections of said anatomical structure by cutting said structure with said blade, wherein said cutting member body includes a curve extending along its transverse axis.

34. A method of structurally enhancing anatomical structures comprising the steps of:
   (a) inserting into adjacent sections of an anatomical structure a blade including a securing mechanism to attach the blade to an instrument and a cutting member having a body with holes defined therein and transverse edges and proximal and distal ends, wherein said cutting member includes a corrugated cutting edge defined along a distalmost edge of said body between said transverse edges and said cutting member body includes a detachment mechanism to detach said cutting member from said securing mechanism; and
   (b) detaching said cutting member from said securing mechanism via said detachment mechanism to enable said blade to couple said adjacent sections.

35. A method of attaching a corrugated blade to an instrument, wherein said instrument includes a handle having a blade attachment member including plural blade engagement sections with each section having at least one hole defined therein, and wherein said blade includes at least one opening defined within a corrugation recess, said method comprising the steps of:
   (a) positioning said blade between said engagement sections such that said openings within said corrugation recess and said openings of said engagement sections are aligned; and
   (b) inserting a fastener through said aligned openings to secure said blade to said instrument.

36. A method of attaching a corrugated blade to an instrument, wherein said instrument includes a handle having a slot defined at its distal end, said method comprising the steps of:
   (a) positioning said corrugated blade within said slot; and
   (b) inserting a fastener through said handle such that said fastener resides within a corrugation recess and forces said blade against walls of said slot to secure said blade to said instrument.

37. A method of attaching a corrugated blade to an instrument, wherein said instrument includes a power tool having a blade attachment member with an engagement mechanism and said blade includes an adapter to interface said power tool engagement mechanism, said method comprising the steps of:
   (a) inserting said adapter of said corrugated blade within said power tool blade attachment member such that said adapter interfaces said engagement mechanism to secure said corrugated blade to said power tool.

38. The method of claim 37 wherein said blade adapter includes an elongated bar attached to and extending from said blade proximal end with an opening defined therein, and step (a) further includes:
   (a.1) inserting said adapter bar of said corrugated blade within said blade attachment member to secure said corrugated blade to said power tool.

39. The method of claim 37 wherein said blade adapter includes an elongated bar attached to and extending from said blade proximal end, wherein said bar includes a plurality of projections extending transversely from said bar, and step (a) further includes:
   (a.1) inserting said adapter bar of said corrugated blade within said power tool blade attachment member to secure said blade to said power tool.

* * * * *